United States Patent
Li et al.

(10) Patent No.: US 10,646,464 B2
(45) Date of Patent: May 12, 2020

(54) METHODS FOR TREATING CANCER

(71) Applicant: Boston Biomedical, Inc., Cambridge, MA (US)

(72) Inventors: Chiang Jia Li, Cambridge, MA (US); Youzhi Li, Westwood, MA (US); Wei Li, Wayland, MA (US); Matthew Hitron, West Roxbury, MA (US); Yuan Gao, Belmont, MA (US)

(73) Assignee: Boston Biomedical, Inc., Cambridge, MA (US)

( * ) Notice: Subject to any disclaimer, the term of this patent is extended or adjusted under 35 U.S.C. 154(b) by 0 days.

(21) Appl. No.: 15/981,406

(22) Filed: May 16, 2018

(65) Prior Publication Data

US 2018/0333385 A1 Nov. 22, 2018

Related U.S. Application Data

(60) Provisional application No. 62/507,353, filed on May 17, 2017.

(51) Int. Cl.
| | |
|---|---|
| *A61K 31/343* | (2006.01) |
| *A61K 31/337* | (2006.01) |
| *A61P 35/04* | (2006.01) |
| *A61P 35/00* | (2006.01) |

(52) U.S. Cl.
CPC .......... *A61K 31/343* (2013.01); *A61K 31/337* (2013.01); *A61P 35/00* (2018.01); *A61P 35/04* (2018.01); *A61K 2300/00* (2013.01)

(58) Field of Classification Search
CPC .... A61K 31/337; A61K 31/343; A61K 45/06; A61P 35/00; A61P 35/04
See application file for complete search history.

(56) References Cited

U.S. PATENT DOCUMENTS

| | | | |
|---|---|---|---|
| 2,472,133 A | 6/1949 | Viktor et al. |
| 5,595,721 A | 1/1997 | Kaminski et al. |
| 5,677,095 A | 10/1997 | Kikuchi et al. |
| 5,736,137 A | 4/1998 | Anderson et al. |
| 5,846,534 A | 12/1998 | Waldmann et al. |
| 6,235,883 B1 | 5/2001 | Jakobovits et al. |
| 6,337,346 B1 | 1/2002 | Lee et al. |
| 6,395,773 B1 | 5/2002 | Hirai et al. |
| 6,682,736 B1 | 1/2004 | Hanson et al. |
| 6,828,337 B2 | 12/2004 | Belloni et al. |
| 6,984,720 B1 | 1/2006 | Korman et al. |
| 6,994,862 B2 | 2/2006 | Jeong et al. |
| 7,019,147 B1 | 3/2006 | Barth et al. |
| 7,090,843 B1 | 8/2006 | Francisco et al. |
| 7,169,901 B2 | 1/2007 | Baca et al. |
| 7,422,739 B2 | 9/2008 | Anderson et al. |
| 7,435,797 B2 | 10/2008 | Lowman et al. |
| 7,538,234 B2 | 5/2009 | Iida et al. |
| 7,560,111 B2 | 7/2009 | Kao et al. |
| 7,572,442 B2 | 8/2009 | Thorpe et al. |
| 7,691,977 B2 | 4/2010 | Fuh et al. |
| 7,758,859 B2 | 7/2010 | Fuh et al. |
| 7,807,798 B2 | 10/2010 | Jakobovits et al. |
| 7,824,679 B2 | 11/2010 | Hanson et al. |
| 7,910,104 B2 | 3/2011 | Carr et al. |
| 7,910,752 B2 | 3/2011 | Tokuda et al. |
| 7,943,743 B2 | 5/2011 | Korman et al. |
| 8,008,449 B2 | 8/2011 | Korman et al. |
| 8,101,177 B2 | 1/2012 | Fuh et al. |
| 8,119,775 B2 | 2/2012 | Moretta et al. |
| 8,143,379 B2 | 3/2012 | Hanson et al. |
| 8,168,179 B2 | 5/2012 | Honjo et al. |
| 8,217,149 B2 | 7/2012 | Irving et al. |
| 8,354,509 B2 | 1/2013 | Carven et al. |
| 8,440,190 B2 | 5/2013 | Waldmann et al. |
| 8,529,902 B2 | 9/2013 | Teeling et al. |
| 8,617,554 B2 | 12/2013 | Roberts et al. |
| 8,623,357 B2 | 1/2014 | Waldmann et al. |
| 8,685,394 B2 | 4/2014 | Jure-Kunkel |
| 8,716,452 B2 | 5/2014 | Jure-Kunkel |
| 8,779,108 B2 | 7/2014 | Queva et al. |
| 8,784,815 B2 | 7/2014 | Korman et al. |
| 8,802,091 B2 | 8/2014 | Johnson et al. |
| 8,877,803 B2 | 11/2014 | Jiang et al. |
| 8,900,587 B2 | 12/2014 | Carven et al. |
| 8,952,136 B2 | 2/2015 | Carven et al. |
| 8,977,803 B2 | 3/2015 | Horn et al. |

(Continued)

FOREIGN PATENT DOCUMENTS

| | | |
|---|---|---|
| AU | 2015218436 | 9/2015 |
| AU | 2017203239 | 6/2017 |

(Continued)

OTHER PUBLICATIONS

Yoh et al., "Weekly Chemotherapy with Cisplatin, Vincristine, Doxorubicin, and Etoposide Is an Effective Treatment for Advanced Thymic Carcinoma", 2003, Cancer, 98(5), pp. 926-931. (Year: 2003).*

Lemma et al., "Phase II Study of Carboplatin and Paclitaxel in Advanced Thymoma and Thymic Carcinoma", May 2011, Journal of Clinical Oncology, 29(15), pp. 2060-2065. (Year: 2011).*

Yau-Lin Tseng, "Thymic carcinoma: A rare cancer requiring special attention", 2011, Formosan Journal of Surgery, vol. 44, Issue 4, Aug. 2011, pp. 136-140. (Year: 2011).*

Hubbard et al., "Napabucasin: An Update on the First-in-Class Cancer Sternness Inhibitor", 2017, Drugs, 77(10), pp. 1091-1103. (Year: 2017).*

(Continued)

*Primary Examiner* — My-Chau T. Tran

(74) *Attorney, Agent, or Firm* — Fish & Richardson P.C.

(57) ABSTRACT

Methods for treating advanced thymoma and thymic carcinoma in a subject comprising administering and kits comprising at least one paclitaxel compound and at least one compound of formula (I) (2-acetylnaphtho[2,3-b]furan-4,9-dione) as disclosed herein.

6 Claims, 10 Drawing Sheets

(56) References Cited

U.S. PATENT DOCUMENTS

| | | |
|---|---|---|
| 8,981,065 B2 | 3/2015 | Moretta et al. |
| 9,062,113 B2 | 6/2015 | Weber et al. |
| 9,084,766 B2 | 7/2015 | Li et al. |
| 9,096,672 B2 | 8/2015 | Weber et al. |
| 9,102,725 B2 | 8/2015 | Korman et al. |
| 9,150,530 B2 | 10/2015 | Jiang et al. |
| 9,150,656 B2 | 10/2015 | Johnson et al. |
| 9,212,224 B2 | 12/2015 | Cogswell et al. |
| 9,220,776 B2 | 12/2015 | Sharma et al. |
| 9,328,345 B2 | 5/2016 | Li et al. |
| 9,381,184 B2 | 7/2016 | Li et al. |
| 9,730,909 B2 | 8/2017 | Li et al. |
| 9,732,055 B2 | 8/2017 | Li et al. |
| 9,745,278 B2 | 8/2017 | Li et al. |
| 9,834,532 B2 | 12/2017 | Jang et al. |
| 10,377,731 B2 | 8/2019 | Li et al. |
| 2004/0006009 A1 | 1/2004 | Larsen et al. |
| 2004/0092428 A1 | 5/2004 | Chen et al. |
| 2004/0138140 A1 | 7/2004 | Xu et al. |
| 2004/0138189 A1 | 7/2004 | Sebti et al. |
| 2005/0010060 A1 | 1/2005 | Blokhin et al. |
| 2005/0049207 A1 | 3/2005 | Kaufmann |
| 2006/0019256 A1 | 1/2006 | Clarke et al. |
| 2006/0099251 A1 | 5/2006 | Johannsson |
| 2006/0142271 A1 | 6/2006 | Muller et al. |
| 2006/0222696 A1 | 10/2006 | Okada et al. |
| 2006/0247318 A1 | 11/2006 | Song et al. |
| 2006/0252674 A1 | 11/2006 | Peritt et al. |
| 2006/0279011 A1 | 12/2006 | Palakodaty et al. |
| 2007/0009532 A1 | 1/2007 | Sikic et al. |
| 2007/0060521 A1 | 3/2007 | Jove et al. |
| 2007/0123502 A1 | 5/2007 | Turkson et al. |
| 2007/0207980 A1 | 9/2007 | Salama et al. |
| 2007/0238770 A1 | 10/2007 | Gougoutas et al. |
| 2009/0042977 A1 | 2/2009 | Tokuda et al. |
| 2010/0297118 A1 | 11/2010 | Macdougal et al. |
| 2010/0310503 A1 | 12/2010 | Li et al. |
| 2011/0008331 A1 | 1/2011 | Triebel |
| 2011/0112180 A1 | 5/2011 | Jiang et al. |
| 2012/0077986 A1 | 3/2012 | Iida et al. |
| 2012/0252763 A1 | 10/2012 | Li et al. |
| 2013/0028944 A1 | 1/2013 | Li et al. |
| 2013/0034591 A1 | 2/2013 | Li et al. |
| 2015/0018410 A1 | 1/2015 | Jiang et al. |
| 2015/0183756 A1 | 7/2015 | Li et al. |
| 2015/0307609 A1 | 10/2015 | Lonberg et al. |
| 2016/0030384 A1 | 2/2016 | Li et al. |
| 2016/0060344 A1 | 3/2016 | Narwal et al. |
| 2016/0220494 A1 | 8/2016 | Stroyer et al. |
| 2016/0271099 A1 | 9/2016 | Li et al. |
| 2017/0197932 A1 | 7/2017 | Jiang et al. |
| 2017/0319537 A1 | 11/2017 | Li et al. |
| 2018/0030021 A1 | 2/2018 | Li et al. |
| 2018/0030022 A1 | 2/2018 | Li et al. |
| 2018/0098959 A1 | 4/2018 | Li et al. |
| 2018/0140572 A1 | 5/2018 | Li et al. |
| 2018/0250260 A1 | 9/2018 | Li et al. |
| 2018/0250261 A1 | 9/2018 | Li et al. |
| 2019/0076392 A1 | 3/2019 | Li et al. |
| 2019/0135773 A1 | 5/2019 | Li et al. |
| 2019/0224157 A1 | 7/2019 | Li et al. |
| 2019/0231735 A1 | 8/2019 | Li et al. |
| 2019/0375723 A1 | 12/2019 | Ban et al. |

FOREIGN PATENT DOCUMENTS

| | | |
|---|---|---|
| CA | 2107806 | 4/1994 |
| CA | 2959931 | 9/2011 |
| CA | 2959951 | 9/2011 |
| EP | 0466094 | 1/1992 |
| EP | 0592366 | 4/1994 |
| EP | 1897540 | 3/2008 |
| EP | 2436669 | 4/2012 |
| EP | 3108750 | 12/2016 |
| JP | 63196576 | 8/1988 |
| JP | 04139177 | 5/1992 |
| JP | H09-249560 | 9/1997 |
| JP | 1121284 | 1/1999 |
| JP | 1165141 | 3/1999 |
| JP | 2004224802 | 8/2004 |
| JP | 2007145680 | 6/2007 |
| JP | 2012092083 | 5/2012 |
| JP | 2016016973 | 2/2016 |
| JP | 6199787 | 9/2017 |
| JP | 2019110987 | 6/2019 |
| SU | 1049490 | 10/1983 |
| WO | WO 99/62909 | 12/1999 |
| WO | WO 00/44774 | 8/2000 |
| WO | WO 2000/059473 | 10/2000 |
| WO | WO 01/23372 | 4/2001 |
| WO | WO 01/168139 | 9/2001 |
| WO | WO 2004/026253 | 4/2004 |
| WO | WO 2004/046120 | 6/2004 |
| WO | WO 2004/045593 | 8/2004 |
| WO | WO 2005/033048 | 4/2005 |
| WO | WO 2005/056055 | 6/2005 |
| WO | WO 2005/058829 | 6/2005 |
| WO | WO 2005/110477 | 11/2005 |
| WO | WO 2006/014359 | 2/2006 |
| WO | WO 2006/018627 | 2/2006 |
| WO | WO 2006/052712 | 5/2006 |
| WO | WO 2006/056399 | 6/2006 |
| WO | WO 2006/065894 | 6/2006 |
| WO | WO 2006/091837 | 8/2006 |
| WO | WO 2006/098355 | 9/2006 |
| WO | WO 2006/113790 | 10/2006 |
| WO | WO 2007/056470 | 5/2007 |
| WO | WO 2007/061880 | 5/2007 |
| WO | WO 2007/074347 | 7/2007 |
| WO | WO 2007/087129 | 8/2007 |
| WO | WO 2007/092620 | 8/2007 |
| WO | WO 2007/095753 | 8/2007 |
| WO | WO 2007/100640 | 9/2007 |
| WO | WO 2007/115269 | 10/2007 |
| WO | WO 2008/077062 | 6/2008 |
| WO | WO 2008/094321 | 8/2008 |
| WO | WO 2009/036059 | 3/2009 |
| WO | WO 2009/036099 | 3/2009 |
| WO | WO 2009/036101 | 3/2009 |
| WO | WO 2009/060282 | 5/2009 |
| WO | WO 2010/027827 | 3/2010 |
| WO | WO 2011/008331 | 1/2011 |
| WO | WO 2011/066342 | 6/2011 |
| WO | WO 2011/084694 | 7/2011 |
| WO | WO 2011/116398 | 9/2011 |
| WO | WO 2011/116399 | 9/2011 |
| WO | WO 2012/119265 | 9/2012 |
| WO | WO 2013/166618 | 11/2013 |
| WO | WO 2013/172918 | 11/2013 |
| WO | WO 2013/173223 | 11/2013 |
| WO | 2014169078 | 10/2014 |
| WO | WO 2015/155673 | 10/2015 |
| WO | WO 2015/190489 | 12/2015 |
| WO | WO 2016/044234 | 3/2016 |
| WO | WO 2016/157052 | 10/2016 |
| WO | WO 2016/168856 | 10/2016 |
| WO | WO 2016/168857 | 10/2016 |
| WO | WO 2016/196935 | 12/2016 |
| WO | WO 2017/132049 | 8/2017 |
| WO | WO 2017/013865 | 5/2018 |
| WO | WO 2018/096401 | 5/2018 |
| WO | WO 2018/183089 | 10/2018 |
| WO | 2018213424 | 11/2018 |
| WO | WO 2017/164379 | 1/2019 |

OTHER PUBLICATIONS

National Center for Biotechnology Information. PubChem Database. Napabucasin, CID=10331844, https://pubchem.ncbi.nlm.nih.gov/compound/Napabucasin (accessed on Jan. 6, 2020; Create: Oct. 25, 2006) (Year: 2006).*

"International Application Serial No. PCT US2018 032937, International Search Report dated Aug. 24, 2018", 5 pgs.

(56) References Cited

OTHER PUBLICATIONS

"International Application Serial No. PCT US2018 032937, Written Opinion dated Aug. 24, 2018", 7 pgs.

Chang, "Activation of STAT3 in thymic epithelial tumours correlates with tumour type and clinical behavior", J Pathol, (2006), 224-33.

Igawa, S, "Efficacy of chemotherapy with carboplatin and paclitaxej for unresectable thymic carcinoma", Lung Cancer, Elsevier, Amsterdam, Nl, vol. 67 No. 2, 194-197.

Joleen, Hubbard M, "Napabucasin: An Update on the First-in-Class Cancer Stemness Inhibitor", Drugs, vol. 77, No. 10, (Jul. 2017), 1091-1103.

Michael, Ried, "State of the art diagnostic tools and innovative therapies for treatment of advanced thymoma and thymic carcinoma", European Journal of Cardio-Thoracic Surgery, (Dec. 15, 2015), 1545-1552.

Al-Hajj and Clarke, "Self-renewal and solid tumor stem cells," Oncogene, 2004, 23(43):7274-82.

Capsugel, "Technical Reference File: Hard Gelatin Capsules," 4th Edition, 57 pages.

International Preliminary Report on Patentability in Application No. PCT/US2018/023827, dated Oct. 1, 2019, 13 pages.

International Preliminary Report on Patentability in Application No. PCT/US2018/032937, dated Nov. 19, 2019, 9 pages.

Panigrahi "Gelucire: A versatile polymer for modified release drug delivery system," Future Journal of Pharmaceutical Sciences, Jun. 2018, 4(1):102-108.

Shen, et al., "Synthesis and antiproliferative activity of indolizinophthalazine-5,12-dione derivatives, DNA topoisomerase IB inhibitors," European Journal of Medicinal Chemistry, 2010, 45(9):3938-3942.

Achcar et al., "Expression of Activated and Latent Signal Transducer and Activator of Transcription 3 in 303 Non-Small Cell Lung Carcinomas and 44 Malignant Mesotheliomas: Possible Role for Chemotherapeutic Intervention," Arch Pathol Lab Med., 2007, 131(9):1350-60.

Ailles and Weissman, "Cancer Stem Cells in Solid Tumors," Curr Opin Biotechnol, 2007, 18(5):460-466.

Ajani et al., "Cancer Stem Cells: The Promise and the Potential," Semin Oncol., Apr. 2015, 42(1):S3-17.

Alas, S, "Inhibition of Constitutive STAT3 Activity Sensitizes Resistant Non-Hodgkin's Lymphoma and Multiple Myeloma to Chemotherapeutic Drug-Mediated Apoptosis", Clin Cancer Res, 2003, 9(1):316-26.

Al-Hajj, M., et al., "Prospective Identification of Tumorigenic Breast Cancer Cells", Proc. Natl. Acad. Sci. USA, Apr. 1, 2003, 100(7):3983-3988.

Alvarez et al., "Genome-wide analysis of STAT target genes: elucidating the mechanism of STAT-mediated oncogenesis," Cancer Biology & Therapy, 2004,3(11):1045-1050.

Alvarez et al., "Identification of a genetic signature of activated signal transducer and activator of transcription 3 in human tumors," Cancer Res., 2005, 65(12):5054-62.

Alvi, "Functional and Molecular Characterization of Mammary Side Population Cells," Breast Cancer Res, 2003, 5(1):R1-R8.

Amin, "Selective inhibition of STAT3 induces apoptosis and G(1) cell cycle arrest in ALK—positive anaplastic large cell lymphoma", Oncogene, 2004, 23(32):5426-5434.

Anderson, "The Process of Structure-Based Drug Design," Chem and Biol, 2003 10:787-797.

Anonymous, "POR cytochrome p450 oxidoreductase [*Homo sapiens*(human)]-Gene-NCBIOfficial Symbol Official Full Name," Jul. 1, 2019, retrieved on Aug. 21, 2019, retrieved from URL <URL:https://www.ncbi.nlm.nih.gov/gene?Db=gene&Cmd= DetailsSearch&Term=5447>, pp. 1-17.

Aoki et al., "Inhibition of STAT3 signaling induces apoptosis and decreases survivin expression in primary effusion lymphoma," Blood, 2003, 101(4):1535-1542.

Arany, "Correlation Between Pretreatment Levels of Interferon Response Genes and Clinical Responses to an Immune Response Modifier (Imiquimod) in Genital Warts," Antimicrob Agents Chemother, 2000, 44(7):1869-73.

Bandhavkar, "Cancer stem cells: a metastasizing menace!," Cancer Medicine, 2016, 5(4):649-655.

Bannwitz et al., "Synthesis and structure-activity relationships of lapacho analogues. 2. Modification of the basic naphtho[2,3-b]furan-4,9-dione, redox activation, and suppression of human keratinocyte hyperproliferation by 8-hydroxynaphtho[2,3-b]thiophene-4,9-diones," J Med Chem., Jul. 24, 2014, 57(14):6226-6239.

Barton et al., "Signal transducer and activator of transcription 3 (STAT3) activation in prostate cancer: Direct STAT3 inhibition induces apoptosis in prostate cancer lines," Mol CancerTher., 2004, 3(1):11-20.

Baumann, "Exploring the Role of Cancer Stem Cells in Radioresistance", Nat. Rev. Cancer. 8.7, (2008), 8(7):545-554.

Becourn et al., "FOLFIRI and Bevacizumab in first-line treatment for colorectal cancer patients: safety, efficacy and genetic polymorphisms," BMC Reasearch Notes, 2014, 7:260.

Benekli et al., "Constitutive activity of signal transducer and activator of transcription 3 protein in acute myeloid leukemia blasts is associated with short disease-free survival," Blood, 2002, 99(1):252-257.

Benkhart, "Role of Stat3 in Lipopolysaccharide-Induced IL-1O gene expression," J Immunol, 2000, 165(3):1612-1617.

Berishaj et al., "Stat3 is tyrosine-phosphorylated through the interleukin-6/glycoprotein 130/Janus kinase pathway in breast cancer," Breast Cancer Res., 2007, 9(3):R32.

Berge et al., "Pharmaceutical Salts," J Pharma Sci, 1977, 66:1-19.

Blaskovich et al., "Discovery of JSI-124 (cucurbitacin I), a selective Janus kinase/signal transducer and activator of transcription 3 signaling pathway inhibitor with potent antitumor activity against human and murine cancer cells in mice," Cancer Res, 2003, 63(6):1270-1279.

Bleau, "New Strategy for the analysis of phenotypic marker antigens in brain tumor-derived neurospheres in mice and humans", Neurosurg Focus, 2008, 24(3-4):E28.

Boman et al., "Human colon cancer stem cells: a new paradigm in gastrointestinal oncology," J Clin Oncol., 2008, 26(17): 2828-2838.

Boman et al., "Cancer stem cells: a step toward the cure," J Clin Oncol 2008, 26(17):2795-99.

Bonnet and Dick, "Human acute myeloid leukemia is organized as a hierarchy that originates from a primitive hematopoietic cell," 1997, 3(7):730-737.

Bonnet, "Normal and leukaemic stem cells", Br J Haematol, (2005), 130(4):469-479.

Borovski, "Cancer stem cell niche: the place to be," Cancer Res 2011, 71(3):634-639.

Bostonbiomedical.com, "Boston Biomedical Data at ASCO 2015 Highlights Potential of Novel Investigational Cancer Stem Cell Pathway Inhibitors BBI608 and BBI503 in Multiple Cancer Types", retrieved on [Jun. 1, 2015] retrieved from URL<http://www.bostonbiomedical.com/boston-biomedical-data-at-asco-2015-highlights-potential-of-novel-investigationsal-cancer-stem-cell-pathway-inhibitors-bbi608-and-bbi-503-in-multiple-cancer-types/>, 4 pages.

Braatz, "Crystallization: Particle Size Control," Encyclopedia of Pharmaceutical Technology, Swarbrick, ed. New York: Informa Healthcare, Third Edition, 2007, 858-871.

Bromberg, "Stat3 as an Oncogene," Cell, 1999, 98(3):295-303.

Bromberg, J., "Stat proteins and oncogenesis," J Clin Invest, 2002, 109(9):1139-1142.

Buettner et al., "Activated STAT signaling in human tumors provides novel molecular targets for therapeutic intervention," Clinical Cancer Research, 2002, 8(4): 945-954.

Burdelya, "Stat3 Activity in Melanoma Cells Affects Migration of Immune Effector Cells and Nitric Oxide—Mediated Antitumor Effects," J Immunol, 174(7):3925-31.

Burke, WM, et al., "Inhibition of Constitutively Active STAT-3 Suppresses Growth of Human Ovarian and Breast Cancer Cells", Oncogene, Nov. 29, 2001, 20(55):7925-7934.

Byrn, "Solid-State Chemistry of Drugs, 2d, Chapter 11 Hydrates and Solvates/Hydrates," 233-247.

(56) References Cited

OTHER PUBLICATIONS

Caira, "Crystalline Polymorphism of Oeganic Compounds, Topics in Chemistry," 1998, 198:163-208.
Campbell, "Cytokine-Mediated Inflammation, Tumorigenesis, and Disease Associated JAKISTA/SOCS Signaling Circuits in the CNS," Brain Res Brain Res Rev, 2005, 48(2): 166-77.
Carson, "Interferon-Alpha-Induced Activation of Signal Transducer and Activator of Transcription Proteins in Malignant Melanoma," Clin Cancer Res, 1998, 4(9):2219-2228.
Catlett-Falcone et al. "Constitutive Activation of Stat3 Signaling Confers Resistance to Apoptosis in Human U266 Myeloma Cells," Immunity, 1999, 10(1):105-115.
Cains, "Classical Methods of Preparation of Polymorphs and Alternative Sold Forms," Polymorphism in Pharmaceutical Solids, 2nd Edition, 2009, 70 pages.
Cesari, "Inflammatory Markers and Onset of Cardiovascular Events: Results from the Health ABC Study," Circulation, 2003 108(19):2317-2322.
Chan et al., "Disruption of Stat3 reveals a critical role in both the initiation and the promotion stages of epithelial carcinogenesis," J. Clin. Invest., 2004, 114:720-728.
Chang et al., "Ealuation of Tumor Cell-Tumor Microenvironment Component Interactions as Potential Predictors of Patient Response to Napabucasin," Mol Can Res., Jul. 1, 2019, 13(7):1429-1434.
Chen et al., "Signal transducer and activator of transcription 3 is involved in cell growth and survival of human rhabdomyosarcoma and osteosarcoma cells," BMC Cancer, 2007, 7:111.
Chen et al., "Constituents of Markhamia Hildebrandtii (Baker) Sprague and their Antitumor Activity", STN Database Accession No. 1986:568912,Chemical Abstracts Service, Columbus, OH XP002662423, Nov. 15, 1986, 2 pgs.
Chen et al., "Stat3 activation in human endometrial and cervical cancers," Br J Cancer., 2007, 96(4):591-599.
Cho-Vega et al., "Suppressor of cytokine signaling 3 expression in anaplastic large cell lymphoma," Leukemia, 2004 18(11):1872-1878.
Clarke, "Self-renewal and solid-tumor stem cells," Biol Blood Marrow Transplant, Feb. 2005, 11(2 suppl 2):14-16.
Clarke, "Cancer Stem Cells—Perspectives on Current Status and Future Directions: AACR Workshop on Cancer Stem Cells," Cancer Research, 2006, 66(19):9339-44.
Clinicaltrials.com, "A Study of BBI603 Administered With Paclitaxel in Adult Patients With Advanced Malignancies", ID NCT01325441, Boston Biomedical, [retrieved on Feb. 19, 2016] Retrieved from URL <http://clinicaltrials.gov/archive/ NCTO 1325441/2011_03_28>, 3 pages.
Clinicaltrials.com, "A Study of BBI608 in Adult Patients with Advanced, Refractory Hematologic Malignancies," ID NCT02352558, Boston Biomedical, [retrieved on Feb. 19, 2016] Retrieved from URL <https://clinicaltrials.gov/ct2/show/NCT02352558?term=BBI608&rank=1>, 5 pages.
Clinicaltrials.com, "A Study of BBI608 in Adult Patients with Advanced Colorectal Cancer," ID NCT01776307, [retrieved Aug. 22, 2019] retrieved from URL <https://clinicaltrials.gov/ct2/show/NCT01776307>, 10 pages.
Clinicaltrials.com, "A Study of BBI608 in Combination with Standard Chemotherapies in Adult Patients with Advanced Gastrointestinal Cancer," ID NCT02024607, Boston Biomedical, [retrieved on Feb. 19, 2016] Retrieved from URL <https://clinicaltrials.gov/ct2/show/NCT02024607?term=bbi608&rank=3>, 7 pages.
Clinicaltrials.com, "A Study of BBI608 in Combination with Temozolomide in Adult Patients with Recurrent or progressed Glioblastoma," ID NCT02315534, [retrieved on Feb. 19, 2016] Retrieved from URL <https://clinicaltrials.gov/ct2/show/NCT02315534?term=BBI608&rank=10.
Clinicaltrials.com, "A Study of BBI608 in Combination with Standard Chemotherapies in Adult Patients with Pancreatic Cancer," ID NCT02231723, [retrieved Mar. 19, 2019] Retrieved from URL <https://clinicaltrials.gov/ct2/show/NCT02231723>, 15 pages.
Clinicaltrials.com, "A Study of BBI608 Administered in Combination With Immune Checkpoint Inhibitors in Adult Patients With Advanced Cancers," ID NCT02467361, [retrieved Aug. 16, 2019] Retreieved from URL <https://clinicaltrials.gov/ct2/show/NCT02467361>, 9 pages.
Collins, "Prospective Identification of Tumorigenic Prostate Cancer Stem Cells," Cancer Res, 2005, 65(23):10946-10951.
Colman et al., "Effect of a small molecule inhibitor of the JAK2/STAT3 pathway on self-renewal of glioblastoma stem cells," Journal of Clinical Oncology, 2008, 26:15S.
Colman de Saizarbitoria et al., "Bioactive furonaphtoquinones from Tabebuia barbata (Bignoniaceae)," Acta Cient Venez, 1997, 48(1):42-46.
Corvinus et al., "Persistent STAT3 activation in colon cancer is associated with enhanced cell proliferation and tumor growth," Neoplasia, 2005, 7(6):545-555.
Dalerba, "Phenotypic Characterization of Human Colorectal Cancer Stem Cells," Proc Natl Acad Sci USA, Jun. 2007, 104(24):10158-10163.
Darnell et al., "Validating Stat3 in cancer therapy", Nature Medicine, Jun. 2005, 11(6):595-596.
De Araujo et al. "STAT3 expression in salivary gland tumours," Oral Oneal., 2008, 44(5):439-45.
De Boer, "Liposomal doxorubicin in metastatic breast cancer," Breast Cancer Res., 1999, 2:66629-66631.
Dean et al., "Tumour Stem Cells and Orig Resistance", Nat Rev Cancer, 2005, 5:275-284.
"Definition of Cancer", MedicineNet.com., [Online] retrieved from the internet: <http://www.medterms.com>, (2004).
General Correspondence from Boston Biomedical to Department of Health and Human Services Investigational New Drug Application, Napabucasin, IND 100887, Serial No. 0179, Dec. 22, 2017, 8 pages.
Danishefsky et al., "Stereospecific total syntheses of dl-coriolin and dl-coriolin B," J of Am Chem Soc., 1981, 103(12):3460-3467.
Defant et al., "Regioselectivity in the Multi-Component Synthesis of Indolizinoquinoline-5,12-dione Derivatives," European Journal of Organic Chemistry, Sep. 2006, 18:4201-4210.
Desmond et al., "The Synthetic Furanonaphthoquinone Induces Growth Arrest, Apoptosis and Differentiation in a Variety of Leukaemias and Multiple Myeloma Cells." Brit. J. Haematol., 2005, 131(4):520-529.
Diaz et al., "Furanonaphthoquinones from *Tabebuia ochracea* ssp. neochrysanta", J. Nat. Prod., 1996, 59(4):423-424.
Diaz et al., "Activation of stat3 in primary tumors from high-risk breast cancer patients is associated with elevated levels of activated SRC and survivin expression," Clin Cancer Research, 2006, 12(1):20-8.
Dien et al., "Signal Transducers and Activators of Transcription-3 up-Regulates Tissue Inhibitor of Metalloproteinase-1 Expression and Decreases Invasiveness of Breast Cancer," Am J of Pathology., 2006, 169(2):633-642.
Doyle and Ross, "Multidrug Resistance Mediated by the Breast Cancer Resistance Protein BCRP (ABCG2)", Oncogene, 2003, 22(47):7340-7358.
Epling-Burnette et al., "Inhibition of STAT3 signaling leads to apoptosis of leukemic large granular lymphocytes and decreased Mcl-1 expression," J. Clin. Invest., 2001, 107(3):351-362.
Elzagheid, Adam, et al., "Nuclear [beta]-catenin expression as a prognostic factor in advanced colorectal carcinoma", World Journal of Gastroenterology, Jun. 28, 2008, 14(24):3866-3871.
Eyler, "Survival of the Fittest: Cancer Stem Cells in Therapeutic Resistance and Angiogenesis", J. Clin. Oneal., 2008, 26(17):2839-2845.
Eyong, et al., "Semisynthesis and antitumoral activity of 2-acetylfuranonaphthoquinone and other naphthoquinone derivatives from lapachol", Bioorganic & Medicinal Chemistry Letters, 2008, 18(20):5387-5390.
Fagerholm, "Experimental Estimation of the Effective Unstirred Water Layer Thickness in the Human Jejunum, and its Importance in Oral Drug Absorption," Eur. J. Pharm. 1995, 3:247-253.
Faloppi et al, "The correlation between LDH serum levels and clinical outcome in advanced biliary tract cancer patients treated with first line chemotherapy," Scientific Reports, 2016, 6:24136.

(56) References Cited

OTHER PUBLICATIONS

Farina, F., et al., "La Reaccion De La 2-Acetil-1.4-Benzoouinona V Ouinonas Analogas Con Tioles. Aplicacion a La Sintesis De Tiofenouinonas", Analesde Quimica, 1976, (72):902-908.

Feldmann, M, "Role of Cytokines in Rheumatoid Arthritis", Annu Rev Immunol, 1996, 14:397-440.

Fotsing, "Identification of an Anti-Inflammatory Principle from the Stem Bark of Millettia Versicolor," Planta Med, Aug. 1, 2003, 69(8):767-70.

Frank, "ABCB5-Mediated Doxorubicin Transport and Chemoresistance in Human Malignant Melanoma," Cancer Res, 2005, 65(10):4320-4333.

Frank, "STAT3 as a Central Mediator of Neoplastic Cellular Transformations," Cancer Lett., 2007, 251(2):199-210.

Fu, "STAT3 in Immune Responses and Inflammatory Bowel Disease," Cell Res, 16(2):214-219(2006).

Furtek et al, "Strategies and Approaches of Targeting STAT3 for Cancer Treatment," ACS Chem. Biol., Jan. 5, 2016, 11(2):308-318.

Furqan, et al., "STAT inhibitors for cancer therapy," J Hematology & Oncology, 2013, 6:90.

Gafner, "Antifungal and Antibacterial Naphthoquinones from Newbouldia Laevis Roots," Phytochemistry., 2007, 42(5):1315-1320.

Gao et al., "Inhibition of STAT3 expression by siRNA suppresses growth and induces apoptosis in laryngeal cancer cells," Acta Pharmacol Sin., 2005, 26(3):377-383.

Gao et al., "Knockdown of Stat3 expression using RNAi inhibits growth of laryngeal tumors in vivo," Acta Pharmacol Sin., 2006, 27(3):347-352.

Gao et al., "Constitutive activation of JAK-STAT3 signaling by BRCA1 in human prostate cancer cells," FEBS Letters, 2001, 488(3):179-184.

Garcia et al., "Constitutive activation of Stat3 in fibroblasts transformed by diverse oncoproteins and in breast carcinoma cells," Cell Growth Differ, 1997, 8(12):1267-1276.

Garcia, "Constitutive activation of Stat3 by the Src and JAK tyrosine kinases participates in growth regulation of human breast carcinoma cells", Oncogene, 2001, 20:2499-2513.

Goodell, "Isolation and Functional Properties of Murine Hematopoietic Stem Cells That are Replicating in Vivo," J. Exp. Med. 183. 4(1996):1797-1806.

Gormann, "Furanonaphthoquinones, Atraric Acid and a Benzofuran from the Stem Barks of Newbouldia Laevis," Phytochemistry, 64.2(2004):583-587.

Gowrishankar et al., "Inducible but Not Constitutive Expression of PD-L1 in Human Melanoma Cells Is Dependent on Activation of NF-κB," Plos One., Apr. 6, 2015, pp. 1-19.

Gritsko et al. "Persistent activation of stat3 signaling induces survivin gene expression and confers resistance to apoptosis in human breast cancer cells," Clinical Cancer Research Center, 2006, 12(1):11-19.

Gupta, et al., "Cancer stem cells: mirage or reality?" Nat Med, Sep. 2009, 15(9):1010-1012.

Hisahiro, Hagiwara, et al., "Domino Michael-O-alkylation reaction: one-pot synthesis of 2,4-diacylhydrofuran derivatives and its application to antitumor naphthofuran synthesis", J. Chem. Soc., Perkin Trans., 2001, 22:2946-2957.

Hagiwara, et al., "Tandem nucleophilic reaction leading to hydrofurans: application to one-pot synthesis of antitumor naphthofuran natural product", Heterocycles, 1999, (51)3:497-500.

Hagler et al., "Sophorolipids Decrease IgE Production in U266 Cells by Downregulation of BSAP (Pax5), TLR-2, STAT3 and IL-6," J Allergy Clin Immunol, 119(1):S263.

Haleblian, "Pharmaceutical Applications of Polymorphism," J. Pharm. Sci. Aug. 1969, 58(8):911-29.

Hambardzumyan, "Radiation Resistance and Stem-Like Cells in Brain Tumors," Cancer Cell, 2006, 10(6):454-456.

Han Li., "Unusual Naphthoquinone Derivatives from the Twigs of Avicennia Marina," J. Nat. Prod., 2007, 70:923-927.

Harada, T, "Increased Expression of STAT3 in SLE T Cells Contributes to Enhanced Chemokine-Mediated Cell Migration", Autoimmunity, 2006, 40:1-8.

Haraguchi, "Characterization of a Side Population of Cancer Cells from Human Gastrointestinal System," Stem Cells, 2006, 24(3):506-513.

Harris, "Cutting Edge: An in Vivo Requirements for STAT3 Signaling in TH17 Development and TH17—dependent Autoimmunity," J Immunol, 179(7):4313-4317.

Hart, H, "Organic Chemistry: A Short Course", Houghton Mifflin Harcourt College Division, Boston, Massachusetts, 9th Edition, 1995, 279.

Haura et al., "Activated epidermal growth factor receptor-Stat-3 signaling promotes tumor survival in vivo in non-small cell lung cancer," Clin Cancer Res, 2005, 11(23):8288-8294.

He et al., "Prodrugs of Phosphonates, Phosphinates, and Phosphates," Prodrugs, 2007, pp. 224-264.

Hirai et al., "Furanonaphthoquinone derivatives as antiviral, antifungal and antibacterial agents," STN Database Accession No. 1997:632811, 1 pg.

Hirai, "Furanonaphthoquinone Analogs Possessing Preferential Antitumor Activity Compared to Normal Cells," Cancer Detection and Prevention, 1999 23(6):539-550.

Hironaka, Shuichi, et al., "Weekly paclitaxel as second-line chemotherapy for advanced or recurrent gastric cancer", Gastric Cancer, Springer-Verlag, to, vol. 9, No. 1, (Feb. 1, 2006), 14-18.

Ho, "Side Population in Human Lung Cancer Cell Line and Tumors is Enriched with Stem-Like Cancer Cells," Cancer Res., 2007, 67(10):4827-4833.

Holtick et al., "STAT3 is essential for Hodgkin lymphoma cell proliferation and is a target of tyrphostin AG17 which confers sensitization for apoptosis," Leukemia., 2005, 19(6):936-944.

Horiguchi et al., "Activation of signal transducer and activator of transcription 3 in renal cell carcinoma: a study of incidence and its association with pathological features and clinical outcome," The Journal of Urology, 2002, 168(2):762-765.

Hsiao et al., "Constitutive activation of STAT3 and STAT5 is present in the majority of nasopharyngeal carcinoma and correlates with better prognosis," Br J Cancer., 2003, 89(2):344-349.

Huang, M., et al., "Constitutive Activation of Stat 3 Oncogene Product in Human Ovarian Carcinoma Cells", Gynecologic Oncology, 2000, 79(1):67-73.

Ikegawa et al., "Furonaphthoquinone derivatives as antiviral, antifungal and antibacterial agents," STN Database Accession No. 1989:560194, 2 pages.

International Search Report and Written Opinion in International Application No. PCT/US2008/075848, dated May 14, 2009, 8 pages.

International Search Report and Written Opinion in International Application No. PCT/US2008/075906, dated Dec. 8, 2008, 10 pages.

International Search Report and Written Opinion in International Application No. PCT/US2016/028179, dated Oct. 20, 2016, 11 pages.

International Search report and Written Opinion in International Application No. PCT/US2017/014163, dated Jul. 10, 2017, 13 pages.

International Search Report and Written Opinion in International Application No. PCT/US2008/075903, dated Feb. 24, 2009, 12 pages.

International Search Report and Written Opinion in International Application No. PCT/US2011/029281, dated Aug. 12, 2011, 10 pages.

International Search Report and Written Opinion in International Application No. PCT/US2011/029283, dated May 17, 2011, 8 pages.

International Search Report and Written Opinion in International Application No. PCT/US2014/033566, dated Dec. 16, 2014, 18 pages.

International Search Report and Written Opinion in International Application No. PCT/US2016/028177, dated Jul. 20, 2016, 10 pages.

(56) References Cited

OTHER PUBLICATIONS

International Search Report and Written Opinion in International Application No. PCT/US2016/028178, dated Aug. 9, 2016, 12 page.
International Search Report and Written Opinion in International Application No. PCT/US2017/063734, dated Jan. 25, 2018, 13 pages.
International Search Report and Written Opinion in International Application No. PCT/IB2017/001573, dated May 16, 2018, 16 pages.
International Search Report and Written Opinion in International Application No. PCT/US2018/023827, dated Aug. 20, 2018, 20 pages.
International Search Report and Written Opinion in International Application No. PCT/US2019/034658, dated Sep. 10, 2019, 15 pages.
International Preliminary Report on Patentability in International Application No. PCT/US2008/075906, dated Mar. 16, 2010, 10 pages.
International Preliminary Report on Patentability in International Application No. PCT/US2017/014163, dated Jul. 24, 2018, 8 pages.
International Preliminary Report on Patentability in International Application No. PCT/US2008/075903, dated Mar. 16, 2010, 11 pages.
International Preliminary Report on Patentability in International Application Serial No. PCT/US2011/029281, dated Sep. 25, 2012, 7 pages.
International Preliminary Report on Patentability in International Application No. PCT/US2011/029283, dated Sep. 25, 2012, 6 pages.
International Preliminary Report on Patentability in International Application No. PCT/US2014/033566, dated Oct. 13, 2015, 13 pages.
International Preliminary Report on Patentability in International Application No. PCT/US2016/028177, dated Oct. 17, 2017, 7 pages.
International Preliminary Report on Patentability in International Application No. PCT/US2016/028178, dated Oct. 17, 2017, 8 pages.
International Preliminary Report on Patentability in International Application No. PCT/US2017/063734, dated Jun. 4, 2019, 8 pages.
International Preliminary Report on Patentability in International Application No. PCT/IB2017/001573, dated May 28, 2019, 10 pages.
International Preliminary Report on Patentability in Application No. PCT/US2008/075848, dated Mar. 16, 2010, 6 pgs.
Invitation to Pay Additional Fees and, Where Applicable, Protest Fee in International Application No. PCT/IB2017/001573, dated Mar. 13, 2018, 15 pages.
Invitation to Pay Additional Fees and, Where Applicable, Protest Fee in International Application No. PCT/US2018/023827, dated Jun. 18, 2018, 15 pages.
Inagaki et al., "Synthesis and Cytotoxicity on Human Leukemia Cells of Furonaphthoquinones Isolated from Tabebuia Plants," Chemical and Pharmaceutical Bulletin, 61(6):670-673.
Ishihara and Hirano, "IL-6 in Autoimmune Disease and Chronic Inflammatory Proliferative Disease," Cytokine Growth Factor Rev, 2002, 13(4-5):357-368.
Itoh et al., "Requirement of STAT3 activation for maximal collagenase-1 (MMP-1) induction by epidermal growth factor and malignant characteristics in T24 bladder cancer cells," Oncogene, 2006, 25(8):1195-1204.
Itoigawa, "Cancer Chemopreventive Activity of Naphthoquinones and Their Analogs from Avicennia Plants," Cancer Letters, 2001, 174(2):135-139.
Ivashkiv and Tassiulas, "Can SOCS make Arthritis Better?," J Clin Invest, 2003, 111(6):795-797.
Iwamaru et al., "A novel inhibitor of the STAT3 pathway induces apoptosis in malignant glioma cells both in vitro and in vivo," Oncogene, 2007, 26(17):2435-44.

Ji et al., "Clinicopathological implications of NQ01 overexpression in the prognosis of pancreatic adenocarcinoma," Oncol Lett., Mar. 7, 2017, 13(5):2996-3002.
Johnson et al., "Abrogation of Signal Transducer and Activator of Transcription 3 Reactivation After Src Kinase Inhibition Results in Synergistic Antitumor Effects." Clin. Cancer Res. 13.14(2007):4233-4244.
Johnston et al. "STAT3 Signaling: Anticancer Strategies and Challenges." Mol. Interv. 11.1(2011):18-26.
Jones, "Cancer Stem Cells: Are We Missing the Target?," J Natl Cancer Inst, 2004, 96(8):583-585.
Jonker et al., "Napabucasin versus placebo in refractory advanced colorectal cancer: a randomized phase 3 trial." Lancet Gastroenterol Hepatol., Apr. 2018 2018, 3(4):263-270.
Jordan, "Cancer stem cells," N Engl J Med., Sep. 21, 2006, 355(12):1253-1261.
Kamel-Reid et al, "Engraftment of immune-deficient mice with human hematopoietic stem cells," Science, Dec. 23, 1988, 242:1706-1709.
Kanda et al., "STAT3 is constitutively activated and supports cell survival in association with survivin expression in gastric cancer cells," Oncogene, 2004, 23(28):4921-4929.
Kang, "A New Route to Naphtho[2,3-b]furan-4,9-Diones from Thia-Substituted 1,4-Naphthoquinones," J. Chem. Soc. Perkin Trans., 1990, 441-445.
Katoh et al., "STAT3-Induced WNT5A Signaling Loop in Embryonic Stem Cells, Adult Normal Tissues, Chronic Persistent Inflammation, Rheumatoid Arthritis and Cancer," Int. J. Mol. Med., 2007, 19(2):273-278.
Kijima et al., "STAT3 activation abrogates growth factor dependence and contributes to head and neck squamous cell carcinoma tumor growth in vivo," Cell Growth Diff., 2002, 13:355-362.
Kikuchi, T., et al., "Electrophotographic Photosensitive Member", STN Database Accession No. 1992:245248, Chemical Abstracts Service, Columbus, OH XP002661424, (Jun. 15, 1992), 5 DOS.
Kim et al, "A specific STAT3-binding peptide exerts antiproliferative effects and antitumor activity by inhibiting STAT3 phosphorylation and signaling," Cancer Res., Apr. 15, 2014, 74(8):2144-2151.
Kim et al., "Inhibition of Signal Transducer and Activator of Transcription 3 Activity Results in Down-Regulation of Survivin Following Irradiation," Mol. Cancer Thera. 2006, 5(11):2659-2665.
Kim, "JAK-STAT Signaling Mediates Gangliosides-Induced Inflammatory Responses in Brain Microglial Cells," J Biol Chem, 2002, 277(43):40594-40601.
Klein et al., "Increased Expression of Stem Cell Markers in Malignant Melanoma", Mod Pathol., 2007, 20:102-107.
Kortylewski, M, et al., "Inhibiting STAT3 Signaling in the Hematopoietic System Elicits Multicomponent Antitumor Immunity", Nat Med, 11(12):1314-1321.
Kobayashi et al., "One-Pot Synthesis of Naphtho[2,3-b]furan-4,9-diones by Sequential Coupling/Ring Closure Reactions", Tetrahedron Letters, 1997, 38(5):837-840.
Kobayashi et al., "An Improved Method for the Preparation of 4,7-Dioxo-4,7-dihydrobenzo[b]thiophene-2-carboxylates from 2-Acyl-1,4-benzoquinones and Mercaptoacetates,", Heterocyclesm, 2001, 55(21):2423-2429.
Kondo, "Persistence of a Small Subscription of Cancer Stem-Like Cells in the C6 Glioma Cell Line," Proc Natl Acad Sci USA, 2004, 101(3):781-786.
Konnikova et al., "Knockdown of STAT3 expression by RNAi induces apoptosis in astrocytoma cells," BMC Center 2003, 3:23.
Koyanagi, "A Facile Synthesis of 2-Acteylnaphtho[2,3-b]furan-4,9-Dione," Journal of Heterocyclic Chemistry, 1995, 32:1289-1291.
Koyanagi, "A New Synthetic of 2-Substituted Naphtho[2,3-b]furan-4,9-Dione," Journal of Heterocyclic Chemistry, 1997, 34:407-412.
Koyama et al., "Micellar Electrokinetic Chromatography (MEKC) Separation of Furanonaphthoquinones from Tabebuia Impetiginosa," Chem. Pharm. Bull. (Tokyo), Jun. 2000, 48(6):873-875.
Krause, "Rheumatoid Arthritis Synoviocyte Survival is Dependent on Stat3," J Immunol, 2002, 169(11):6610-6.
Kumar, "Clinical Trials and Progress with Paclitaxel in Ovarian Cancer," International Journal of Women's Health 2010, 2:411-427.

(56) References Cited

OTHER PUBLICATIONS

Kusaba et al., "Expression of p-STAT3 in human colorectal adenocarcinoma and adenoma; correlation with clinicopathological factors," Journal of Clinical Pathology, 2005, 58(8):833-838.
Laatsch, "Synthese von Maritinon und anderen 8,8'-Bijuglonen," Liebigs Annalen der Chemie, 1985, 12:2420-2442 English Abstract.
Lai et al.,"STAT3 is activated in a subset of the Ewing sarcoma family of tumours," J Pathol. 2006, 208(5):624-632.
Lai, "Signal Transducer and Activator of Transcription-3 Activation Contributes to High Tissue Inhibitor of Metalloproteinase-1 Expression in Anaplastic Lymphoma Kinase-Positive Anaplastic Large Cell Lymphoma," Am J Pathol, 2004, 164(6):2251-58.
Lande, "The Relationship Between Membrane Fluidity and Permeabilities to Water, Solutes, Ammonia, and Protons," J. Gen. Physiol, 1995, 106:67-84.
Larochelle et al, "Identification of primitive human hematopoietic cells capable of repopulating NOD/SCID mouse bone marrow: implications for gene therapy," Nat. Med., Dec. 1996, 2:1329-1337.
Lassman et al., "STAT3 mRNA and protein expression in colorectal cancer: effects on STAT3-inducible targets linked to cell survival and proliferation," J Clin Pathol. 2007, 60(2): 173-9.
Lau et al., "Inhibition of Stat3 activity by YC-1 enhances chemosensitivity in hepatocellular carcinoma," Cancer Biol Ther., 2007, 6(12):1900-7.
Le et al, "PD-1 Blockade in Tumors with Mismatch-Repair Deficiency," N. Engl. J. Med., Jun. 25, 2015, 372:2509-2520.
Lee, "Efficient Synthesis of Cytotoxic Furonaphthoquinone Natural Products," Synthetic Communications, 2001, 31(3):381-386.
Leong et al., Targeted inhibition of Stat3 with a decoy oligonucleotide abrogates head and neck cancer cell growth Proc Natl Acad Sci USA, 2003, 100(7):4138-43.
Li et al., "Abstract LB-253: Inhibition of Stemness by BBI608 is Sufficient to Suppress Cancer Relapse and Metastasis", Cancer Research. AACR 106th Annual Meeting 2015, Apr. 18-22, 2015, Philadelphia, PA, published Aug. 1, 2015, 75(15 Supplement).
Li et al., "Autocrine-mediated activation of STAT3 correlates with cell proliferation in breast carcinoma lines," J. Biol. Chem. 2002, 277:17397-17405.
Li et al., "Inhibition of growth and metastasis of human hepatocellular carcinoma by antisense oligonucleotide targeting signal transducer and activator of transcription 3," Clin Cancer Res., 2006, 12(23):7140-8.
Li, "Identification of Pancreatic Cancer Stem Cells," Cancer Res, 2007, 67(3):1030-1037.
Li et al., "Feedback activation of STAT3 mediates trastuzumab restistance via upregulation of MUC1 and MUC4 expression," OncoTarget, Jun. 26, 2014, 5(18):8317-8329.
Li et al., "Suppression of cancer relapse and metastasis by inhibiting cancer stemness", Proceedings of the National Academy of Sciences, Jan. 20, 2015, 112(6):1839-1844.
Liu et al., "Enantio- and Diastereoselective Intermolecular Stetter Reaction of Glyoxamide and Alkylidene Ketoamides," Organic Letters., 2009, 11(13):2856-2859.
Libby et al., "Inflammation and Atherosclerosis," Circulation, 2002, 105(9):1135-1143.
Lim, "Stat3 Contributes to Keloid Pathogenesis via Promoting Collagen Production, Cell Proliferation and Migration," Oncogene, 2006, 25(39):5416-5425.
Lin, L, et al., "STAT3 is Necessary for Proliferation and Survival in Colon Cancer-Initiating Cells", Cancer Res, 71(23):7226-7237.
Lin et al., "STAT signaling in the pathogenesis and treatment of leukemias," Oncogene, May 15, 2000, 19(21):2496-2504.
Lin et al., "Constitutive activation of JAK3/STAT3 in colon carcinoma tumors and cell lines: inhibition of JAK3/STAT3 signaling induces apoptosis and cell cycle arrest of colon carcinoma cells," Am J Pathol, 2005, 167:969-980.
Lin et al., "Significance of the expression of phosphorylated signal transducer and activator of transcription-3, -Akt, and -cyclin D1 in angiosarcoma," J. Derm. Sci., 2007, 48(1):64-66.
Lin et al., "Significance of the expression of phosphorylated-STAT3, -Akt, and -ERK1/2 in several tumors of the epidermis," J. Derm. Sci., 2007, 48(1):71-73.
Ling, "Mesenchymal Stem Cells Overexpressing IFN—Inhibit Breast Cancer Growth and Metastases through Stat3 Signaling in a Syngeneic Tumor Model," Cancer Microenviron, 2010, 3(1):83-95.
Lipinski, "Experimental and Computational Approaches to Estimate Solubility and Permeability in Drug Discovery and Development Settings," Adv. Drug Deliv. Rev., 2001, 46(1-3):3-26.
Liou et al., "Reactive oxygen species in cancer," Free Radic Res., May 2010, 44(5):479-496.
Liu et al., "Expression and clinical significance of COX-2, p-Stat3, and p-Stat5 in esophageal carcinoma," Ai Zheng, 2007, 26(5):458-62 [English Abstract].
Lobo et al., "The biology of cancer stem cells," Annu Rev Cel Cev Biol., 2007, 23:675-699.
Lopes et al., "Synthesis of Dimethoxyfuranonaftoquinones," Synthetic Communications, Oct. 1, 1988, 18(14):1731-1742.
Lopes, "Efficient Synthesis of Cytotoxic Quinones: 2-Actey1-4H,9H-naphtho[2,3-b]furan-4, 9-Dione (6) and (:t)-2-(1-Hydroxyethyl)-4H,9H-naphtho[2,3-b]furan-4,9-Dione (7)," Journal of Heterocyclic Chemistry, 1984, 21:621-622.
Lovato, "Constitutive STAT3 Activation in Intestinal T Cells from Patients with Crohn's Disease," J Biol Chem, 2003, 278(19):16777-16781.
McCune et al, "The SCID-hu mouse: murine model for the analysis of human hematolymphoid differentiation and function," Science, Sep. 23, 1988, 241:1632-1639.
Ma et al., "Constitutive activation of Stat3 signaling pathway in human colorectal carcinoma," World J. Gastroent., 2004, 10(11):1569-1573.
Ma, "Identification and Characteristic of Tumorigenic Liver Cancer Stem/Progenitor Cells," Gastroenterology, 2007, 132(7):2542-2556.
Manolagas, "Role of Cytokines in Bone Resorption," Bone, 1995, 17(2 Suppl):63S-67S.
Masayuki et al., "Cytotoxic Activity toward KB Cells of 2-Substituted Naphtho[2,3-b]furan-4, 9-Diones and Their Related Compounds," Biosci. Biotechnol. Biochem., 2006, 70(4): 1009-1012.
Masuda et al., "Constitutive activation of signal transducers and activators of transcription 3 correlates with cyclin D1 overexpression and may provide a novel prognostic marker in head and neck squamous cell carcinoma," Cancer Res. (2002), 62(12):3351-5.
Matsumoto et al., "Individual Formulations Nature and Preparation Method," Medicine Manual, Mar. 20, 1989, 1st Edition:80, translation 5 pages.
Maruyama, A., et al., "Electrophotographic Photoreceptor, Process Cartridge and Electrophotographic Apparatus Using Same", STN Database Accession No. 1999:157137 Chemical Abstracts Service, Columbus, OH XP002661425, (Mar. 10, 1999), 3 pgs.
Migone, T.-S., et al., "Constitutively Activated Jak-STAT Pathway in T Cells Transformed With HTLV-I", Science, Jul. 7, 1995, 269(5220):79-81.
Ministry of Health of the Russian Federation, "Guidelines: For the Experimental(Preclinical) Investigation of New Pharmaceutical Substances," Moscow, 2000, p. 111.
Mizoguchi et al., Journal of Neuropathology and Experimental Neurology, 2006, 65(12):1181-1188.
Mora et al., "Constitutive activation of Stat3 in human prostate tumors and cell lines: direct inhibition of Stat3 signaling induces apoptosis of prostate cancer cells," Cancer Res, 2002 62(22):6659-6666.
Morikawa et al., "STAT3 Expression, Molecular Features, Inflammation Patterns, and Prognosis in a Database of 724 Colorectal Cancers," Clinical Cancer Research, Mar. 15, 2011, 17(6):1452-1462.
Morrissette, "High-Throughput Crystallization: Polymorphs, Salts, Co-Crystals and Solvates of Pharmaceutical Solids," Adv. Drug Delivery Rev. 2004, 56:275-300.
Muller et al., "Potential antipsoriatic agents: lapacho compounds as potent inhibitors of HaCaT cell growth," J. Nat. Prod., 1999, 62:1134-1136.

(56) References Cited

OTHER PUBLICATIONS

Naciuk et al., "Exploitation of a tuned oxidation with N-haloimides in the synthesis of caulibugulones A-D," J Org Chem., May 17, 2013, 78(10):5026-5030.
Nielsen et al., "Inhibition of constitutively activated Stat3 correlates with altered Bcl-2/Bax expression and induction of apoptosis in mycosis fungoides tumor cells," Leukemia, 1999, 13(5):735-738.
Ning et al., "Signal transducer and activator of transcription 3 activation is required for Asp(816) mutant c-Kit-mediated cytokine-independent survival and proliferation in human leukemia cells," Blood, 2001, 97:3559-3567.
Nishi et al., "Retrospective analysis of the international standard-dose FOLFIRI (plus bevacizumab) regimen in Japanese patients with unresectable advanced or recurrent colorectal carcinoma," International Journal of Clinical Oncology, Oct. 2011, 16(5):488-493.
Niu et al., "Gene therapy with dominant-negative Stat3 suppresses growth of the murine melanoma B16 tumor in vivo," Cancer Res., 1999, 15;59(20):5059-5063.
Niu et al., "Roles of activated Src and Stat3 signaling in melanoma tumor cell growth," Oncogene, 2002, 21(46):7001-7010.
Niu et al., "Constitutive Stat3 activity up-regulates VEGF expression and tumor angiogenesis,"Oncogene, 2002, 21(13):2000-2008.
No Author, "International Research Congress on Natural Product as Medicinal Agents", Strasbourg—France, Jul. 6-11, Planta Med, Jul. 1980, 39(3):194-196.
Oettle et al., "Paclitaxel as weekly second-line therapy in patients with advanced pancreatic carcinoma," Anticancer Drugs, 2000, 11(8):635-638.
Oh et al., "Implications of NQ01 in cancer therapy," BMB Reports, Nov. 30, 2015, 48(11):609-617.
Ohta, "Regiospecific Synthesis of 2-Substituted Furanonaphthoquinones," Journal of Heterocyclic Chemistry, Jul. 1, 2000, 37:731-734.
Orshal and Khalil, "Interteukin-6 Mediated Relaxation and Enhances Impairs Endothelium-Dependent NO-cGMP-Contraction in Systemic Vessels of Pregnant Rats," Am J Physiol Regul Integr Comp Physiol, 2004, 286(6):1013-1023.
Paridaens et al., "Paclitaxel Versus Doxorubicin as First-Line Single-Agent Chemotherapy for Metastatic Breast Cancer: a European Organization for Research and Treatment of Cancer Randomized Study with Cross-Over," J. Clin. Oneal. Feb. 2000; 18(4):724-33.
Patil Sharad et al., "NIR-emitting quinone-fused coumarin dyes: aqueous mediated, catalyst free sythesis and their optical properties," Tetrahedron Letters, Elsevier, Jun. 20, 2016, 57(29):3100-3104.
Pedranzini et al., "Stat3 is required for the development of skin cancer," J. Clin. Invest., 2004, 114(5):619-622.
Penning et al., "Synthesis and biological evaluation of the 1,5-diarylpyrazole class of cyclooxygenase-2 inhibitors: identification of 4-[5-(4-methylphenyl)-3-(trifluoromethyl)-1H-pyrazol-1-yl]benze nesulfonamide (SC-58635, celecoxib)," J Med Chem., Apr. 25, 1997, 40(9):1347-1365.
Perez-Sacau, et al., "Synthesis and Pharmacophore Modeling of Naphthoquinone Derivatives with Cytotoxic Activity in Human Promyelocytic Leukemia HL-60 Cell Line", J. Med. Chem., Feb. 2007, 50(4):696-706.
Peraza-Sanchez, "Cytotoxic Constituents of the Roots of Ekmanianthe Longiflora," American Chemical Society Publication—Journal of Natural Products, (2000), 63:492-495.
Pereira et al., "Invasion-Associated MMP-2 and MMP-9 are up-Regulated Intracellularly in Concert with Apoptosis Linked to Melanoma Cell Detachment," Clinical and Experimental Metastasis, 2005, 22:285-295.
Pfitzner, et al., "The Role of STA Ts in Inflammation and Inflammatory Diseases", Curr Pharm Des, Sep. 2004, 10(23):2839-2850.
Pinzon-Guzman, "Protein kinase C regulates rod photoreceptor differentiation through modulation of STAT3 signaling", Adv Exp Med Biol, 2010, 664:21-28.
Pillai et al., "Effects of transient overexpression or knockdown of cytochrome P450 reductase on reactive oxygen species generation and hypoxia reoxygenation injury in liver cells," Dept of Pharma Sci., Dec. 2011, 38(12):846-853.
Poli et al., "STAT3-mediated metabolic reprograming in cellular transformation and implications for drug resistance," Frontiers in Oncology, Jun. 8, 2015, 5(121):6 pages.
Ponti, "Isolation and in Vitro Propagation of Tumorigenic Breast Cancer Cells with Stem/Progenitor Cell Properties," Cancer Res, 2005, 65(13):5506-11.
Porter "New insights into the role of cytochrome P450 reductase (POR) in microsomal redox biology," Acta Pharmaceutical Sinica., 2012, 2(2):102-106.
Price, "Computational Methodologies: Toward Crystal Structure and Polymorph Prediction," Polymorphism in Pharmaceutical Solids, CRC Press, Boca Raton, FL, 2009, 2nd edition, 31 pages.
Prince, "Identification of a Subpopulation of Cells with Cancer Stem Cell Properties in Head and Neck Squamous Cell Carcinoma," Proc Natl Acad Sci USA, 2007, 104(3):973-978.
Punjabi et al., "Persistent activation of STAT3 by latent Kaposi's sarcoma-associated herpesvirus infection of endothelial cells", J Viral, (2007), 81(5):2449-2458.
Puthier et al., "IL-6 Up-Regulates MCL-1IN Human Myeloma Cells through JAK/STAT rather than ras/MAP Kinase Pathway," Eur J lmmunol, 1999, 29(12):3945-3950.
Qui et al., "RNA interference-mediated signal transducers and activators of transcription 3 gene silencing inhibits invasion and metastasis of human pancreatic cancer cells," Cancer Sci. 2007, 98(7):1099-1106.
Qiuwen et al, "Evaluation of the Potential Cancer Chemotherapeutic Efficacy of Natural Product Isolates Employing in Vivo Hallow Fiber Tests," J. Nat. Prod. 2002, 65(6):842-850.
Rahaman et al., "Inhibition of constitutively active Stat3 suppresses proliferation and induces apoptosis in glioblastoma multiforme cells," Oncogene, 2002, 21(55):8404-8413.
Rao and Kingston, "Plant Anticancer Agents. XII. Isolation and Structure Elucidation of New Cytotoxic Quinones from Tabebuia Cassinoides," Journal of Natural Products, 1982, 45(5):600-604.
Rawat et al., "Constitutive activation of STAT3 is associated with the acquisition of an interleukin 6-independent phenotype by murine plasmacytomas and hybridomas," Blood, 2000, 96(10):3514-3521.
Reagan-Shaw, "Dose Translation from Animal to Human Studies Revisited," The FASEB Journal, 2007, 22(3):659-661.
Ricci-Vitiani, "Identification and Expansion of Human Colon-Cancer-Initiating Cells," Nature. 2007, 445(7123):111-115.
Rieber et al., "Relationship of Mc1-1 isoforms, ratio p21WAF1/cyclin A, and Junkinase phosphorylation to apoptosis in human breast carcinomas", Biochemical and Biophysical Research Communications , 2002, 297:943-949.
Rieber et al., "Mc1-1 cleavage and sustained phosphorylation of c-Jun-N-terminal kinase mediate melanoma apoptosis induced by 2-acetyl furanonaphthoquinone," Cancer Biology and Therapy, 2008, 7(8):1206-1211.
Rouhi, "The Right Stuff," Chemical & Engineering News, 81(8):32-35.
Roder, "STAT3 is Constitutively Active in Some Patients with Polycythemia Rubra Vera," Exp Hematol, 2001, 29(6):694-702.
Romano et al, "The therapeutic promise of disrupting the PD-1/PD-L1 immune checkpoint in cancer: unleashing the CD8 T cell mediated anti-tumor activity results in significant, unprecedented clinical efficacy in various solid tumors," J Immunother Cancer., Apr. 21, 2015, 3:15, 5 pages.
Rosen et al., "The role of constitutively active signal transducer and activator of transcription 3 in ovarian tumorigenesis and prognosis," Cancer, 2006, 107(11):2730-2740.
Rowland et al., "Clinical Pharmacokinetics: Concepts and Applications," Lippincott Williams & Wilkins, 1995, 4th edition, Front Matter.
Ryu et al., "Synthesis and antifungal activity of furo[2,3-f]quinolin-5-ols," Bioorg Med Chem Lett., Feb. 1, 2011, 21(3):952.
Sano et al., "STAT3 Links Activated Keratinocytes and Immunocytes Required for Development of Psoriasis in a Novel Transgenic Mouse Model", Nat Med, 2005, 11(1):43-49.

(56) References Cited

OTHER PUBLICATIONS

Savarese et al., "Coexpression of oncostatin M and its receptors and evidence for STAT3 activation in human ovarian carcinomas," Cytokine, 2002, 17(6):324-334.
Schaefer et al., "Constitutive activation of Stat3alpha in brain tumors: localization to tumor endothelial cells and activation by the endothelial tyrosine kinase receptor (VEGFR-2)," Oncogene, 2002, 21(13):2058-2065.
Schatton, "Identification of Cells Initiating Human Melanomas," Nature. 2008, 451(7176):345-349.
Scheper, "Sulindac induces apoptosis and inhibits tumor growth in vivo in head and neck squamous cell carcinoma", Neoplasia, 2007, 9(3):192-199.
Schlette, "Survivin Expression Predicts Poorer Prognosis in Anaplastic Large-Cell Lymphoma," J Clin Oncol, 2004, 22(9):1682-1688.
Scholz et al., "Activated signal transducer and activator of transcription 3 (STAT3) supports the malignant phenotype of human pancreatic cancer", Gastroenterolgy, 2003, 125:891-905.
Schumacher et al., "Reactive Oxygen Species in Cancer: A Dance with the Devil," Cell Press Canc Cell., Feb. 9, 2015, 27(2):156-157.
Sengupta, "Activation of Monocycle Effector Genes and STAT Family Transcription Factors by Inflammatory Synovial Fluid is Independent of Interferon Gamma," J Exp Med, 1995, 181(3):1015-1025.
Shaikh et al., "Streptonigrin. 1. Structure-activity relationships among simple bicyclic analogues. Rate dependence of DNA degradation on quinone reduction potential," J Med Chem., 1986, 29(8):1329-1340.
Shouda, "Induction of the Cytokine Signal Regulator SOCS3/CIS3 as a Therapeutic Strategy for Treating Inflammatory Arthritis," J Clin Invest, 108(12):1781-1788.
Siegel et al.,"NAD(P)H: Quinone Oxidoreductase 1 (NQO1) in the Sensitivity and Resistance to Antitumor Quinones," Biochem Pharmacol., Apr. 15, 2012, 83(8):1033-1040.
Silver et al., "Activated signal transducer and activator of transcription (STAT) 3: localization in focal adhesions and function in ovarian cancer cell motility," Cancer Res. 2004, 64(10):3550-3558.
Simamura et al., "Furanonaphthoquinones Cause Apoptosis of Cancer Cells by Inducing the Production of Reactive Oxygen Species by the Mitochondrial Voltage-Dependent Anion Channel", Cancer Biology & Therapy, Nov. 2006, 5(11):1523-1529.
Simeone-Penney, "Airway Epithelial STAT3 Is Required for Allergic Inflammation in a Murine Model of Asthma," J Immunol, 178(10):6191-6199.
Singh, "Identification of a Cancer Stem Cell in Human Brain Tumors," Cancer Res, 2003, 63(18):5821-5828.
Solorzano et al., "Decreased Glycolytic Metabolism Accelerates Apoptosis in Response to 2-Acetyl Furanonaphthoquinone in K1735 Melanoma Irrespective of BCL-2 Overexpression," Cancer Biol. Ther., Mar. 2005, 4(3):329-335.
Sommer et al., "In vivo activation of STAT3 in cutaneous T-cell lymphoma. Evidence for an antiapoptotic function of STAT3," Leukemia, 2004, 18(7):1288-1295.
Song and Grandis, "STAT Signaling in Head and Neck Cancer," Onogene, 2000, 19(21):2489-2495.
Song et al., "Activation of Stat3 by receptor tyrosine kinases and cytokines regulates survival in human non-small cell carcinoma cells," Oncogene, 2003, 22(27):4150-4165.
Song, "A Low-Molecular-Weight Compound Discovered Through Virtual Database Screening Inhibits Stat3 Function in Breast Cancer Cells," Proc. Natl. Acad Sci. 102(13):4700-4705.
Spiekermann et al., "Constitutive activation of STAT transcription factors in acute myelogenous leukemia," Eur J Haematol, 2001, 67(2):63-71.
Srijiwangsa et al. "Roles of NAD (P) H-Guinone Oxidoreductase 1 (NQO1) on Cancer Progression and Chemoresistance," Journal of Clinical & Experimental Oncology, 2017, 6(4):6 pages.
Steinert, "HPLC Separation and Determination of Naphtho[2,3-b]furan-4,9-Diones and Related Compounds in Extracts of Tabebuia Avellanedae (Bignoniaceae)," J Chromato, 1995, 693:281-287.

Stelmasiak, "Interleukin-6 Concentration in Serum and Cerebrospinal Fluid in Multiple Sclerosis Patients," Med Sci Monit, 2000, 6(6):1104-1108.
Stephens, "A Common Functional Variant in the Interleukin-6 gene is Associated with Increased Body Mass Index in Subjects with Type 2 Diabetes Mellitus," Mol Genet Metab, 2004, 82(2):180-186.
STN Accession No. 1985-141337 CN (141337-87-3 Registry), (May 15, 1992), 1 pg.
STN Accession No. 1986 568912.
STN Accession No. 1987-141337 CN: (141337-85-1 Registry), (May 15, 1992), 1 pg.
STN Accession No. 1989-141337 CN: (141337-89-5 Registry), (May 15, 1992), 1 pg.
STN Accession No. 1990-141337 CN: (141337-90-8 Registry),(May 15, 1992), 1 pg.
STN Accession No. 1992:245248.
STN Accession No. 1997-141337 CN: (141337-97-5 Registry), (May 15, 1992), 1 pg.
STN Accession No. 2002:33229.
STN Accession No. 2002:080446, CN: (80446-02-2 Registry), (Nov. 16, 1984), 1 oa.
STN Accession No. 33-221190,CN: (221190-33-6 Registry), (Apr. 15 1999), 1 pg.
STN Accession No. 32-221190, CN: (221190-32-5 Registry), (Apr. 14, 1999), 1 pg.
STN Accession No. 31-221190, CN: (221190-31-4 Registry), (Apr. 14, 1999), 1 pg.
Stout, "No Cancer", [Online] retrieved from the internet<http://nocancer.blogspot.com/2005/05/14-paudarco.html>, (2005).
Sun et al.,"Comparison of Effects of the Tyrosine Kinase Inhibitors AG957, AG490, and ST1571 on BCR-ASL-Expressing Cells, Demonstrating Synergy Between AG490 and ST1571," Blood, 2001, 97(7):2008-2015.
Szotek, "Ovarian Cancer Side Population Defines Cells with Stem Cell-Like Characteristics and Mullerian Inhibiting Substance Responsiveness," Proc Natl Acad Sci USA, 2006, 103(30):11154-11159.
Takano, et al., "Tumor-specific cytotoxicity and type of cell death induced by naphtho[2,3-b]furan-4,9-diones and related compounds in human tumor cell lines: relationship to electronic structure", Anticancer Research, 2009, 29:455-464.
Taylor, "Technical Data Report for Pau D'Arco," Herbal Secrets of the Rainforest, $2^{nd}$ Edition, 2003.
Tefferi, "Classification, Diagnosis and Management of Myeloproliferative Disorders in the JAK2V617F era," Hamtology Am Soc Hematol Educ Program, 2006, 240-245.
Toyonaga et al., "Blockade of constitutively activated Janus kinase/signal transducer and activator of transcription-3 pathway inhibits growth of human pancreatic cancer," Cancer Lett. 2003, 201(1):107-116.
Trovato et al., "Distinctive expression of STAT3 in papillary thyroid carcinomas and a subset of follicular adenomas," Histol Histopathol., 2003, 18: 393-399.
Tsareva et al., "Signal transducer and activator of transcription 3 activation promotes invasive growth of colon carcinomas through matrix metalloproteinase induction," Neoplasia, 2007, 4:279-291.
Tsutsumi et al., "Phase II Trial of Chemotherapy plus Bevacizumab as Second-Line Therapy for Patients with Metastatic Colorectal Cancer That Progressed on Bevacizumab with Chemotherapy: The Gunma Clinical Oncology Group (GCOG) trial 001 SILK Study," Oncology, Aug. 2012, 83 (3):151-157.
Wang et al., "Effect of STAT3 siRNA-induced inhibition of STAT3 gene expression on the growth and apoptosis of lewis lung cancer cells", J. Clin. Oneal. 2006, 3(6):392-399.
Wang et al., "Small interfering RNA suppression of transducer and activator of transcription 3 (STAT3) signaling pathway: inhibitory effect on proliferation of human esophageal squamous carcinoma cells," Chinese Journal of Pathology, 2007, 36(6):379-383 [English Abstract].
Wang, "Identification of Cancer Stem Cell-Like Side Population Cells in Human Nasopharyngeal Carcinoma Cell Line," Cancer Res, 2007, 67(8):3716-3724.

(56) References Cited

OTHER PUBLICATIONS

Wang, "A Small Amphipathic a-Helical Region is Required for Transcriptional Activities and Proteasome-Dependent Turnover of the Tyrosine-Phosphorylated STATS", EMBO J, 2000, 19(3):392-399.

Wang et al., "Regulation of the Innate and Adaprive Immune Responses by STAT3 Signaling Tumor Cells", Nat Med, 2004, 10(1):48-54.

Watson & Miller, "Elevated levels of members of the STAT family of transcription factors in breast carcinoma nuclear extracts," British Journal of Cancer, 1995, 71(4):840-844.

Weber-Nordt, "Constitutive Activation of STAT Proteins in Primary Lymphoid and Myeloid Leukemia Cells and in Epstein-Barr Virus (EBV)-Related Lymphoma Cell Lines," Blood, 1996, 88(3):809-816.

Wei et al., "Stat3 activation regulates the expression of vascular endothelial growth factor and human pancreatic cancer angiogenesis and metastasis," Oncogene, 2003, 22(3):319-329.

Wermuth, "Molecular Variations Based on Isoteric Replacements," The Practice of Medicinal Chemistry, Academic Press, 1996. pp. 203-237.

Williams, "Two New Cytotoxic Naphthoquinones from Mendoncia Cowanii from the Rainforest of Madagascar," Planta Med., May 2006, 72(6):564-6.

Wyss-Coray, "Inflammation in Alzheimer disease: driving force, bystander or beneficial response?," Nat Med., Sep. 2006, 12(9):1005-1015.

Xie et al., "Activation of stat3 in human melanoma promotes brain metastasis," Cancer Res., 2006, 66(6):3188-3196.

Xie, "STAT3 Activation Regulates the Expression of Matrix Metalloproteinase-2 and Tumor Invasion and Metastasis," Oncogene, 2004, 23(20):3550-3560.

Yakata et al., "Expression of p-STAT3 in human gastric carcinoma: significant correlation in tumour invasion and prognosis," Int J Oncol., 2007, 30(2):437-442.

Yafee, K, "Inflammatory Markers and Cognition in Well-Functioning African American and White Elders", Neurology, 61(1):76-80.

Yamashita et al., "Synthesis and evaluation of bioactive naphthoquinones from the Brazilian medical plant, Tabebuia avellanedae," Bioorganic & Medicinal Chemistry, 2009, 17(17):6286-6291.

Yao et al., "Experimental Study on the Growth Inhibition of Bladder Cancer Cells by Signal Conduction Blocker AG490," J. Clin. Ural., 2006, 21(5):379-382. (English Abstract).

Yardley., "nab-Paclitaxel mechanisms of action and delivery," J Control Release., Sep. 28, 2013, 170(3):365-372.

Yau et al., "Inhibition of Integrin-Linked Kinase by QLT0254 Inhibits Akt-Dependent Pathways and is Growth Inhibitory in Orthotopic Primary Pancreatic Cancer Xenografls," Cancer Res., 2005, 65(4):1497-1504.

Yong Rok Lee, et al., "Ceric Ammonium Nitrate (CAN)—Mediated Oxidative Cycloaddition of 1,3-Dicarbonyls to Conjugated Compounds. Efficient Synthesis of Dihydrofurans, Dihydrofurocoumarins, Dihydrofuroquinolinones, Dihydrofurophenalenones, and Furonaphthoquinone Natural Products", Tetrahedron, 2000, 56(45):8845-8853.

Yoshida et al., "Discovery and preclinical profile of teneligliptin (3-[(2S,4S)-4-[4-(3-methyl-1-phenyl-1H-pyrazol-5-yl)piperazin-1-yl]pyrrolidin-2-ylcarbonyl]thiazolidine): a highly potent, selective, long-lasting and orally active dipeptidyl peptidase IV inhibitor for the treatment of type 2 diabetes," Bioorg Med Chem., Oct. 1, 2012, 20(19):5705-5719.

Yue et al., "Synthesis and evaluation of indenopyrazoles as cyclin-dependent kinase inhibitors. 3. Structure activity relationships at C3(1,2)," J Med Chem., Nov. 21, 2002, 45(24):5233-5248.

Yu, H, "STAT3: Linking Oncogenesis with Tumor Immune Evasion," AACR Annual Meeting, San Diego, CA, Cancer Res (Abstract SY03-03), 68(9 Supp):1-3.

Yu, H., "The STATs of cancer—new molecular targets come of age," R., Nat Rev Cancer, 2004, 4(2):97-105.

Zani, "Furanonaphthoquinones from Tabebuia Ochracea," Phytochemistry, 1991, 30(7):2379-2381.

Zhang, "Intratumoral Delivery and Suppression of Prostate Tumor Growth by Attenuated *Salmonella enterica* Serovar Typhimurium Carrying Plasmid-Based Small Interfering RNAs," Cancer Res, 2007, 67(12):5859-5864.

Zhou et al., "Activation of the PTEN/mTOR/STAT3 Pathway in Breast Cancer Stem-Like Cells is Required for Viability and Maintenance," PNAS., 104(41):16158-16163.

Zhou et al., "Corrections: Activation of the PTEN/mTOR/STAT3 Pathway in Breast Cancer Stem-Like Cells is Required for Viability and Maintenance," PNAS., 2007, 104(49): 19655-19656.

International Preliminary Report on Patentability in Application No. PCT/US2016/028179, dated Oct. 17, 2017, 8 pages.

Okano, "Introduction to Modern Pharmaceuticals," 1987, revised 3rd edition:111, translation 4 pages.

U.S. Appl. No. 16/577,868, filed Sep. 20, 2019, Li et al. (abstract, specification, and claims only), 111 pages.

U.S. Appl. No. 16/586,049, filed Sep. 27, 2019, Li et al. (abstract, specification, and claims only), 110 pages.

U.S. Appl. No. 16/590,495, filed Oct. 2, 2019, Li et al. (abstract, specification, and claims only), 73 pages.

U.S. Appl. No. 16/591,960, filed Oct. 3, 2019, Li et al. (abstract, specification, and claims only), 65 pages.

\* cited by examiner

METHODS FOR TREATING CANCER

CLAIM OF PRIORITY

This application claims the benefit of priority to U.S. Provisional Application Ser. No. 62/507,353, filed on May 17, 2017, which is incorporated herein by reference in its entirety.

BACKGROUND

Disclosed herein are methods comprising administering to a subject a combination comprising a therapeutically effective amount of at least one compound chosen of formula (I) in combination with a therapeutically effective amount of at least one paclitaxel compound chosen from paclitaxel, pharmaceutically acceptable salts thereof, and solvates of any of the foregoing.

The at least one compound of formula (I) is chosen from compounds having formula (I)

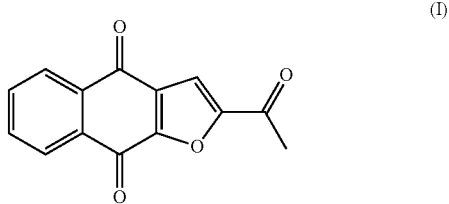 [SMILES: CC(=O)c1cc2c(o1)C(=O)c1ccccc1C2=O]

(I)

prodrugs, derivatives, pharmaceutically acceptable salts of any of the foregoing, and solvates of any of the foregoing.

Cancer fatalities in the United States alone number in the hundreds of thousands each year. Despite advances in the treatment of certain forms of cancer through surgery, radiotherapy, and chemotherapy, many types of cancer are essentially incurable. Even when an effective treatment is available for a particular cancer, the side effects of such treatment can be severe and result in a significant decrease in quality of life.

Most conventional chemotherapy agents have toxicity and limited efficacy, particularly for patients with advanced solid tumors. Conventional chemotherapeutic agents cause damage to non-cancerous as well as cancerous cells. The therapeutic index (i.e., a measure of a therapy's ability to discriminate between cancerous and normal cells) of such chemotherapeutic compounds can be quite low. Frequently, a dose of a chemotherapy drug that is effective to kill cancer cells will also kill normal cells, especially those normal cells (such as epithelial cells and cells of the bone marrow) that undergo frequent cell division. When normal cells are affected by the therapy, side effects such as hair loss, suppression of hematopoiesis, and nausea can occur. Depending on the general health of a patient, such side effects can preclude the administration of chemotherapy, or, at least, be extremely unpleasant and uncomfortable for the patient and severely decrease quality of the remaining life of cancer patients. Even for cancer patients who respond to chemotherapy with tumor regression, cancers often quickly relapse, progress and form more metastasis after initial response to chemotherapy. Such recurrent cancers become highly resistant or refractory to chemotherapeutics. As discussed below, cancer stem cells (CSCs) or cancer cells with high stemness (stemness-high cancer cells) are responsible for the rapid tumor recurrence and resistance to further traditional chemotherapy.

CSCs are believed to possess the following four characteristics:

1. Stemness—As used herein, stemness means the capacity to self-renew and differentiate into cancer cells (Gupta P B et al., *Nat. Med.* 2009; 15(9):1010-1012). While CSCs are only a minor portion of the total cancer cell population (Clarke M F, *Biol. Blood Marrow Transplant.* 2009; 11(2 suppl 2):14-16), they can give rise to heterogeneous lineages of cancer cells that make up the bulk of the tumor (see Gupta et al. 2009). In addition, CSCs possess the ability to mobilize to distinct sites while retaining their stemness properties and thus regrowth of the tumor at these sites (Jordan C T et al. *N. Engl. J. Med.* 2006; 355(12):1253-1261).

2. Aberrant signaling pathways—CSC stemness is associated with dysregulation of signaling pathways, which may contribute to their ability to regrow tumors and to migrate to distant sites. In normal stem cells, stemness signaling pathways are tightly controlled and genetically intact. In contrast, stemness signaling pathways in CSCs are dysregulated, allowing these cells to self-renew and differentiate into cancer cells (see Ajani et al. 2015). Dysregulation of stemness signaling pathways contributes to CSC resistance to chemotherapy and radiotherapy and to cancer recurrence and metastasis. Exemplary stemness signaling pathways involved in the induction and maintenance of stemness in CSCs include: JAK/STAT, Wnt/β-catenin, Hedgehog, Notch, and Nanog (Boman B M et al., *J. Clin. Oncol.* 2008; 26(17):2828-2838).

3. Resistance to traditional therapies—evidence suggests that CSCs possess resistance to conventional chemotherapy and radiation. While the detailed mechanism underlying such resistance is not well understood, the stemness pathways of CSCs (see Boman et al. 2008) together with the tumor microenvironment and aberrant regulation of signaling pathways (Borovski T. et al., *Cancer Res.* 2011; 71(3): 634-639) may contribute to such resistance.

4. Ability to contribute to tumor recurrence and metastasis—although chemotherapy and radiation may kill most of the cells in a tumor, since CSCs are resistant to traditional therapies, the CSCs that are not eradicated may lead to regrowth or recurrence of the tumor either at the primary site or at distant sites (see Jordan et al. 2006). As mentioned above, CSCs may acquire the ability to mobilize to different sites and may maintain stemness at these sites through interactions with the microenvironment, allowing for metastatic tumor growth (see Boman et al. 2008).

The transcription factor Signal Transducer and Activator of Transcription 3 (referred to herein as Stat3) is a member of the Stat family, which are latent transcription factors activated in response to cytokines/growth factors to promote proliferation, survival, and other biological processes. Stat3 is an oncogene that can be activated by phosphorylation of a critical tyrosine residue mediated by growth factor receptor tyrosine kinases, including but not limited to, e.g., Janus kinases (JAKs), Src family kinases, EGFR, Abl, KDR, c-Met, and Her2. Yu, H. Stat3: Linking oncogenesis with tumor immune evasion in AACR 2008 Annual Meeting. 2008. San Diego, Calif. Upon tyrosine phosphorylation, the phosphorylated Stat3 ("pStat3") forms homo-dimers and translocates to the nucleus, where it binds to specific DNA-response elements in the promoters of target genes, and induces gene expression. Pedranzini, L., et al. *J. Clin. Invest.,* 2004. 114(5): p. 619-22.

In normal cells, Stat3 activation is transient and tightly regulated, lasting for example from 30 minutes to several hours. However, Stat3 is found to be aberrantly active in a wide variety of human cancers, including all the major carcinomas as well as some hematologic tumors. Persistently active Stat3 occurs in more than half of breast and lung cancers, colorectal cancers (CRC), ovarian cancers, hepatocellular carcinomas, multiple myelomas, etc., and in more than 95% of head/neck cancers. Stat3 plays multiple roles in cancer progression and is considered to be one of the major mechanisms for drug resistance to cancer cells. As a potent transcription regulator, Stat3 targets genes involved in cell cycle, cell survival, oncogenesis, tumor invasion, and metastasis, such as Bcl-xl, c-Myc, cyclin Dl, Vegf, MMP-2, and survivin. Catlett-Falcone, R., et al. Immunity, 1999. 10(1): p. 105-15; Bromberg, J. F., et al. Cell, 1999. 98(3): p. 295-303; Kanda, N., et al. Oncogene, 2004. 23(28): p. 4921-29; Schlette, E. J., et al. J Clin Oncol, 2004. 22(9): p. 1682-88; Niu, G., et al. Oncogene, 2002. 21(13): p. 2000-08; Xie, T. X., et al. Oncogene, 2004. 23(20): p. 3550-60. It is also a key negative regulator of tumor immune surveillance and immune cell recruitment. Kortylewski, M., et al. Nat. Med., 2005. 11(12): p. 1314-21; Burdelya, L., et al. J. Immunol., 2005. 174(7): p. 3925-31; and Wang, T., et al. Nat. Med., 2004. 10(1): p. 48-54.

Abrogation of Stat3 signaling by using anti-sense oligonucleotides, siRNA, dominant-negative form of Stat3, and/or the targeted inhibition of tyrosine kinase activity causes cancer cell-growth arrest, apoptosis, and reduction of metastasis frequency both in vitro and/or in vivo. Pedranzini, L., et al. J Clin. Invest., 2004. 114(5): p. 619-22; Bromberg, J. F., et al. Cell, 1999. 98(3): p. 295-303; Darnell, J. E. Nat. Med., 2005. 11(6): p. 595-96; and Zhang, L., et al. Cancer Res, 2007. 67(12): p. 5859-64.

Furthermore, Stat 3 may play a role in the survival and self-renewal capacity of CSCs across a broad spectrum of cancers. Therefore, an agent with activity against CSCs may hold great promise for cancer patients (Boman, B. M., et al. J. Clin. Oncol. 2008. 26(17): p. 2795-99).

As discussed above, CSCs are a sub-population of cancer cells (found within solid tumors or hematological cancers) that possess characteristics normally associated with stem cells. These cells can grow faster after reduction of non-stem regular cancer cells by chemotherapy, which may be the mechanism for quick relapse after chemotherapies. In contrast to the bulk of cancer cells, which are non-tumorigenic, CSCs are tumorigenic (tumor-forming). In human acute myeloid leukemia, the frequency of these cells is less than 1 in 10,000. Bonnet, D. and J. E. Dick. Nat. Med., 1997. 3(7): p. 730-37. There is mounting evidence that such cells exist in almost all tumor types. However, as cancer cell lines are selected from a sub-population of cancer cells that are specifically adapted to growth in tissue culture, the biological and functional properties of these cell lines can change dramatically. Therefore, not all cancer cell lines contain CSCs.

CSCs have stem cell properties such as self-renewal and the ability to differentiate into multiple cell types. They persist in tumors as a distinct population and they give rise to the differentiated cells that form the bulk of the tumor mass and phenotypically characterize the disease. CSCs have been demonstrated to be fundamentally responsible for carcinogenesis, cancer metastasis, cancer recurrence, and relapse. CSCs are also called, for example, tumor initiating cells, cancer stem-like cells, stem-like cancer cells, highly tumorigenic cells, or super malignant cells.

CSCs are inherently resistant to conventional chemotherapies, which means they are left behind by conventional therapies that kill the bulk of tumor cells. As such, the existence of CSCs has several implications in terms of cancer treatment and therapy. These include, for example, disease identification, selective drug targets, prevention of cancer metastasis and recurrence, treatment of cancer refractory to chemotherapy and/or radiotherapy, treatment of cancers inherently resistant to chemotherapy or radiotherapy and development of new strategies in fighting cancer.

The efficacy of cancer treatments are, in the initial stages of testing, often measured by the amount of tumor mass they kill off. As CSCs form a very small proportion of the tumor cell population and have markedly different biologic characteristics than their differentiated progeny, the measurement of tumor mass may not select for drugs that act specifically on the stem cells. In fact, CSCs are radioresistant and refractory to chemotherapeutic and targeted drugs. Normal somatic stem cells are naturally resistant to chemotherapeutic agents-they have various pumps (e.g., multidrug resistance protein pump) that efflux drugs, higher DNA repair capability, and have a slow rate of cell turnover (chemotherapeutic agents naturally target rapidly replicating cells). CSCs, being the mutated counterparts of normal stem cells, may also have similar functions that allow them to survive therapy. In other words, conventional chemotherapies kill differentiated (or differentiating) cells, which form the bulk of the tumor that is unable to generate new cells. A population of CSCs that gave rise to the tumor could remain untouched and cause a relapse of the disease. Furthermore, treatment with chemotherapeutic agents may only leave chemotherapy-resistant CSCs, so that the ensuing tumor will most likely also be resistant to chemotherapy. Cancer stem cells have also been demonstrated to be resistant to radiation therapy (XRT). Hambardzumyan, et al. Cancer Cell, 2006. 10(6): p. 454-56; and Baumann, M., et al. Nat. Rev. Cancer, 2008. 8(7): p. 545-54.

Since surviving CSCs can repopulate the tumor and cause relapse, anti-cancer therapies that include strategies against CSCs hold great promise. Jones R J et al., J Natl Cancer Inst. 2004; 96(8):583-585. By targeting CSC pathways, it may be possible to treat patients with aggressive, non-resectable tumors and refractory or recurrent cancers as well as prevent tumor metastasis and recurrence. Development of specific therapies targeting CSC pathways, therefore, may improve the survival and quality of life of cancer patients, especially those patients suffering from metastatic disease. Unlocking this untapped potential may involve the identification and validation of pathways that are selectively important for CSC self-renewal and survival. Though multiple pathways underlying tumorigenesis in cancer and in embryonic stem cells or adult stem cells have been elucidated in the past, pathways for cancer stem cell self-renewal and survival are still sought.

Methods for identification and isolation of CSCs have been reported. The methods used mainly exploit the ability of CSCs to efflux drugs or have been based on the expression of surface markers associated with cancer stem cells.

For example, since CSCs are resistant to many chemotherapeutic agents, it is not surprising that CSCs almost ubiquitously overexpress drug efflux pumps such as ABCG2 (BCRP-1), and other ATP binding cassette (ABC) superfamily members. Ho, M. M., et al. Cancer Res., 2007. 67(10): p. 4827-33; Wang, J., et al. Cancer Res., 2007. 67(8): p. 3716-24; Haraguchi, N., et al. Stem Cells, 2006. 24(3): p. 506-13; Doyle, L. A. and D. D. Ross. Oncogene, 2003. 22(47): p. 7340-58; Alvi, A. J., et al. Breast Cancer Res., 2003. 5(1): p. R1-R8; Frank, N. Y., et al. Cancer Res., 2005. 65(10): p. 4320-33; and Schatton, T., et al. Nature, 2008. 451(7176): p. 345-49. Accordingly, the side population (SP) technique, originally used to enrich hematopoetic and leukemic stem cells, was also employed to identify and isolate CSCs. Kondo, T., et al. Proc. Natl Acad. Sci. USA, 2004. 101(3): p. 781-86. This technique, first described by Goodell et al., takes advantage of differential ABC transporter-dependent efflux of fluorescent dyes such as Hoechst 33342 to define a cell population enriched in CSCs. Doyle, L. A. and D. D. Ross. Oncogene, 2003. 22(47): p. 7340-58; and Goodell, M. A., et al. J. Exp. Med., 1996. 183(4): p. 1797-806. Specifically, the SP is revealed by blocking drug efflux with verapamil, at which point the dyes can no longer be pumped out of the SP.

Efforts have also focused on finding specific markers that distinguish CSCs from the bulk of the tumor. Markers originally associated with normal adult stem cells have been found to also mark CSCs and co-segregate with the enhanced tumorigenicity of CSCs. Commonly expressed surface markers by the CSCs include CD44, CD133, and CD166. Al-Hajj, M., et al. Proc. Natl Acad. Sci. USA, 2003. 100(7): p. 3983-88; Collins, A. T., et al. Cancer Res., 2005. 65(23): p. 10946-51; Li, C., et al. Cancer Res., 2007. 67(3): p. 1030-37; Ma, S., et al. Gastroenterology, 2007. 132(7): p. 2542-56; Ricci-Vitiani, L., et al. Nature, 2007. 445(7123): p. 111-15; Singh, S. K., et al. Cancer Res., 2003. 63(18): p. 5821-28; and Bleau, A. M., et al., Neurosurg. Focus, 2008. 24(3-4): p. E28. Sorting tumor cells based primarily upon the differential expression of these surface marker(s) have accounted for the majority of the highly tumorigenic CSCs described to date. Therefore, these surface markers are validated for identification and isolation of CSCs from the cancer cell lines and from the bulk of tumor tissues.

By using aiRNA (asymmetric RNA duplexes), potent Stat3 selective silencing has been achieved in stemness-high cancer cells. This Stat3 silencing may lead to downregulation of cancer cell stemness, and/or inhibition of stemness-high cancer cell survival and self-renewal.

In some embodiments, the at least one compound of formula (I) is an inhibitor of CSC growth and survival. According to U.S. Pat. No. 8,877,803, the compound of formula (I) inhibits Stat3 pathway activity with a cellular $IC_{50}$ of ~0.25 μM. The at least one compound of formula (I) may be synthesized according to U.S. Pat. No. 8,877,803, for example, Example 13. In some embodiments, the at least one compound of formula (I) is used in a method of treating cancers. According to PCT Patent Application No. PCT/US2014/033566, Example 6, the at least one compound of formula (I) was chosen to enter a clinical trial for patients with advanced cancers. The disclosures of U.S. Pat. No. 8,877,803 and PCT Patent Application No. PCT/US2014/033566 are incorporated herein by reference in their entireties.

We have surprisingly discovered that patients with higher expression levels of Stat3 show prolonged overall survival after treatment with at least one compound of formula (I) in clinical trials. Thus, the higher the level of pStat3 found in a cancer patient before treatment, at least in CRC patients, the higher the overall survival (OS) upon administering a treatment comprising a compound of formula (I).

We also have surprisingly discovered that a treatment combination of at least one compound of formula (I) with at least one paclitaxel compound results in anti-tumor activity in subjects with certain types of cancer that progressed on prior taxane treatment.

In some embodiments, disclosed herein are methods for treating cancer that had progressed on at least one prior taxane regimen comprising administering to a subject in need thereof:

a therapeutically effective amount of at least one compound of formula (I) chosen from compounds having formula (I):

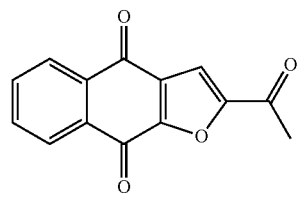

prodrugs, derivatives, pharmaceutically acceptable salts of any of the foregoing, and solvates of any of the foregoing, and a therapeutically effective amount of at least one paclitaxel compound chosen from paclitaxel, pharmaceutically acceptable salt thereof, and solvates of any of the foregoing.

The at least one compound of formula (I) and the at least one paclitaxel compound may be administered to a subject simultaneously and/or sequentially.

The at least one compound of formula (I) may be administered daily in a single or a divided dose. The at least one paclitaxel compound may be administered weekly.

In some embodiments, disclosed herein are methods for resensitizing a subject to at least one prior therapy regimen comprising administering to a subject in need thereof:

a therapeutically effective amount of at least one compound of formula (I) chosen from compounds having formula (I):

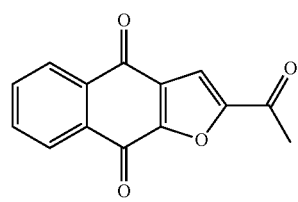

prodrugs, derivatives, pharmaceutically acceptable salts of any of the foregoing, and solvates of any of the foregoing. In some embodiments, the at least one prior therapy regimen is chosen from chemotherapy regimens. In some embodiments, the at least one prior therapy regimen chosen from taxane chemotherapy regimens. In some embodiments, disclosed herein are methods for resensitizing a subject to a taxane chemotherapy regimen comprising administering to a subject in need thereof:

a therapeutically effective amount of at least one compound of formula (I) chosen from compounds having formula (I):

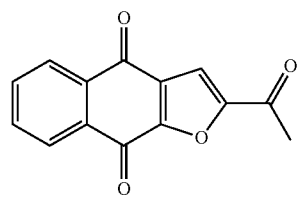

prodrugs, derivatives, pharmaceutically acceptable salts of any of the foregoing, and solvates of any of the foregoing.

In some embodiments, a kit is disclosed that comprises (1) at least one compound chosen from compounds having formula (I), prodrugs, derivatives, pharmaceutically acceptable salts of any of the foregoing, and solvates of any of the foregoing, and (2) at least one paclitaxel compound chosen from paclitaxel, pharmaceutically acceptable salts thereof, and solvates of any of the foregoing, together with instructions for administration and/or use.

Aspects and embodiments of the present disclosure are set forth or will be readily apparent from the following detailed description. It is to be understood that both the foregoing general description and the following detailed description are exemplary and explanatory only, and are not intended to be restrictive of the claims.

DETAILED DESCRIPTION

Figure 1:
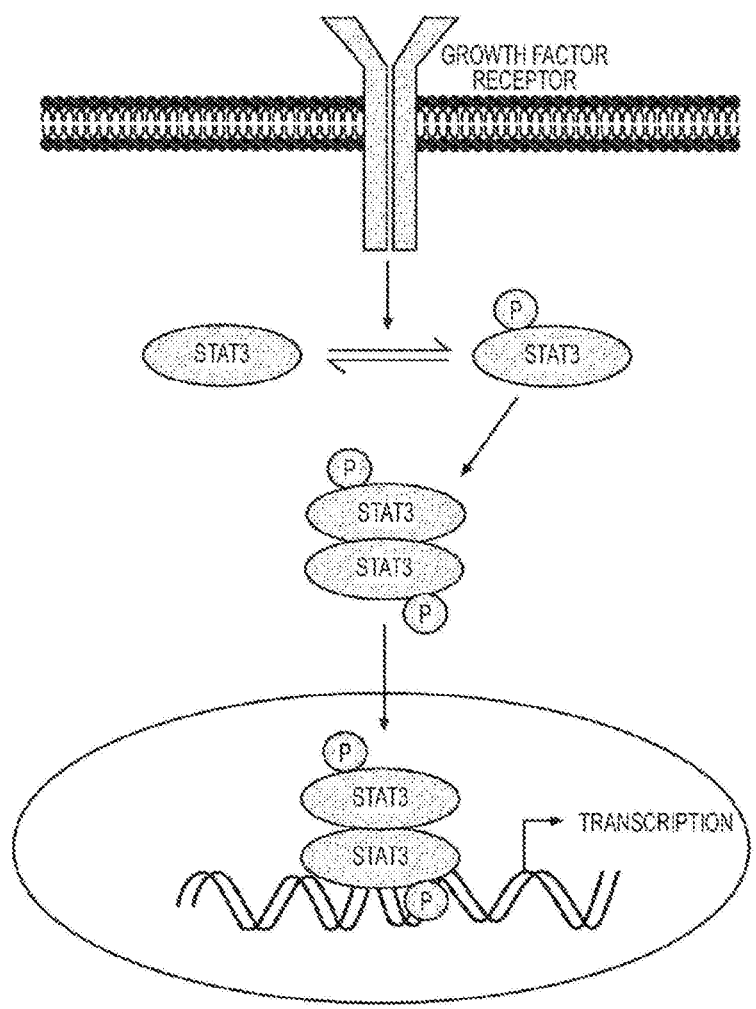
FIG. 1 shows the Stat3 pathway.
Figure 2:
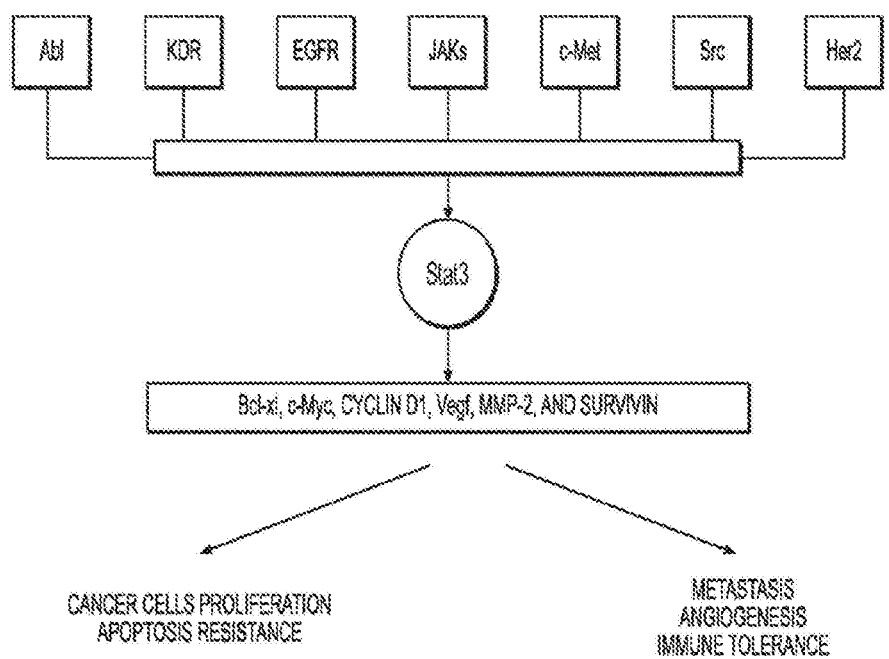
FIG. 2 shows the Stat3 pathway in cancer.
Figure 3:
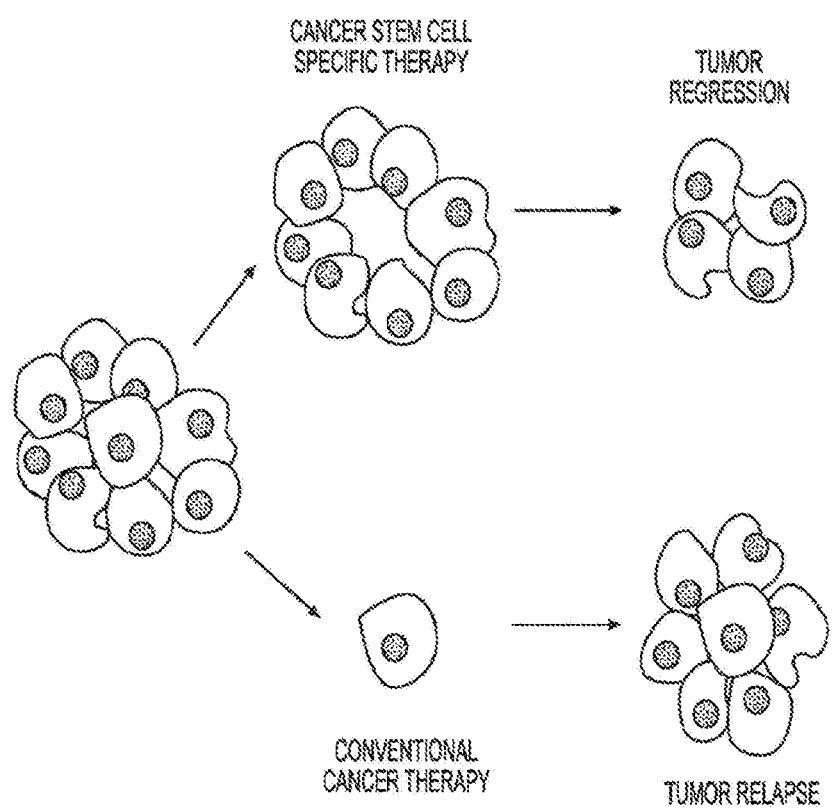
FIG. 3 shows the cancer stem cell specific and conventional cancer therapies.
Figure 4:
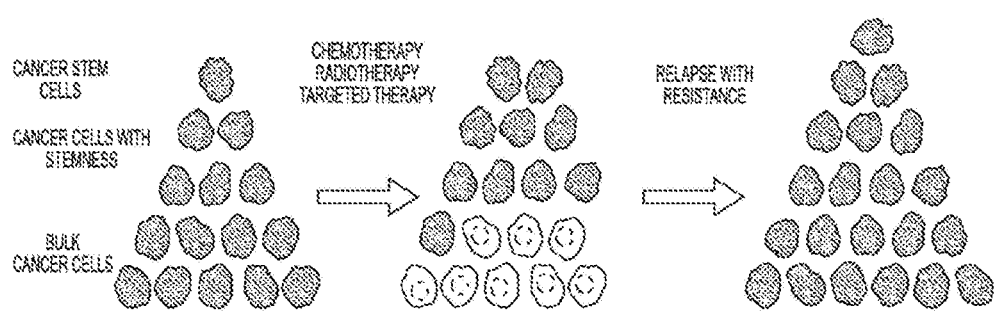
FIG. 4 shows the initiation of relapse and metastases by cancer stem cells and cells with cancer stemness properties following treatment with conventional therapies.

The following are definitions of terms used in the present specification. The initial definition provided for a group or term herein applies to that group or term throughout the present specification individually or as part of another group, unless otherwise indicated.

When the term "about" is used in conjunction with a numerical range, it modifies that range by extending the boundaries above and below those numerical values. In general, the term "about" is used herein to modify a numerical value above and below the stated value by a variance of 20%, 10%, 5%, or 1%. In some embodiments, the term "about" is used to modify a numerical value above and below the stated value by a variance of 10%. In some embodiments, the term "about" is used to modify a numerical value above and below the stated value by a variance of 5%. In some embodiments, the term "about" is used to modify a numerical value above and below the stated value by a variance of 1%.

The terms "administer," "administering," or "administration" are used herein in their broadest sense. These terms refer to any method of introducing to a subject a compound or pharmaceutical composition described herein and can include, for example, introducing the compound systemically, locally, or in situ to the subject. Thus, a compound of the present disclosure produced in a subject from a composition (whether or not it includes the compound) is encompassed in these terms. When these terms are used in connection with the term "systemic" or "systemically," they generally refer to in vivo systemic absorption or accumulation of the compound or composition in the blood stream followed by distribution throughout the entire body.

The term "subject" generally refers to an organism to which a compound or pharmaceutical composition described herein can be administered. A subject can be a mammal or mammalian cell, including a human or human cell. The term also refers to an organism, which includes a cell or a donor or recipient of such cell. In various embodiments, the term "subject" refers to any animal (e.g., a mammal), including, but not limited to humans, mammals and non-mammals, such as non-human primates, mice, rabbits, sheep, dogs, cats, horses, cows, chickens, amphibians, and reptiles, which is to be the recipient of a compound or pharmaceutical composition described herein. Under some circumstances, the terms "subject" and "patient" are used interchangeably herein in reference to a human subject.

The terms "effective amount" and "therapeutically effective amount" refer to that amount of a compound or pharmaceutical composition described herein that is sufficient to effect the intended result including, but not limited to, disease treatment, as illustrated below. In some embodiments, the "therapeutically effective amount" is the amount that is effective for detectable killing or inhibition of the growth or spread of cancer cells, the size or number of tumors, and/or other measure of the level, stage, progression and/or severity of the cancer. In some embodiments, the "therapeutically effective amount" refers to the amount that is administered systemically, locally, or in situ (e.g., the amount of compound that is produced in situ in a subject). The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of cell migration. The specific dose may vary depending on, for example, the particular pharmaceutical composition, subject and their age and existing health conditions or risk for health conditions, the dosing regimen to be followed, the severity of the disease, whether it is administered in combination with other agents, timing of administration, the tissue to which it is administered, and the physical delivery system in which it is carried.

As used herein, the terms "treatment," "treating," "ameliorating," and "encouraging" are used interchangeably herein. These terms refer to an approach for obtaining beneficial or desired results including, but not limited to, therapeutic benefit and/or prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject can still be afflicted with the underlying disorder. For prophylactic benefit, the pharmaceutical composition may be administered to a subject at risk of developing a particular disease, or to a subject reporting one or more of the physiological symptoms of a disease, even though a diagnosis of this disease may not have been made.

The term "cancer" in a subject refers to the presence of cells possessing characteristics typical of cancer-causing cells, such as uncontrolled proliferation, immortality, metastatic potential, rapid growth and proliferation rate, and certain morphological features. Often, cancer cells will be in the form of a tumor or mass, but such cells may exist alone within a subject, or may circulate in the blood stream as independent cells, such as leukemic or lymphoma cells. Examples of cancer as used herein include, but are not limited to, lung cancer, pancreatic cancer, bone cancer, skin cancer, head or neck cancer, cutaneous or intraocular melanoma, breast cancer, uterine cancer, ovarian cancer, peritoneal cancer, colon cancer, rectal cancer, colorectal adenocarcinoma, cancer of the anal region, stomach cancer, gastric cancer, gastrointestinal cancer, gastric adenocarcinoma, adrenocorticoid carcinoma, uterine cancer, carcinoma of the fallopian tubes, carcinoma of the endometrium, carcinoma of the vagina, carcinoma of the vulva, Hodgkin's Disease, esophageal cancer, gastroesophageal junction cancer, gastroesophageal adenocarcinoma, chondrosarcoma, cancer of the small intestine, cancer of the endocrine system, cancer of the thyroid gland, cancer of the parathyroid gland, cancer of the adrenal gland, sarcoma of soft tissue, Ewing's sarcoma, cancer of the urethra, cancer of the penis, prostate cancer, bladder cancer, testicular cancer, cancer of the ureter, carcinoma of the renal pelvis, mesothelioma, hepatocellular cancer, biliary cancer, kidney cancer, renal cell carcinoma, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers. Some of the exemplified cancers are included in general terms and are included in this term. For example, urological cancer, a general term, includes bladder cancer, prostate cancer, kidney cancer, testicular cancer, and the like; and hepatobiliary cancer, another general term, includes liver cancers (itself a general term that includes hepatocellular carcinoma or cholangiocarcinoma), gallbladder cancer, biliary cancer, or pancreatic cancer. Both urological cancer and hepatobiliary cancer are contemplated by the present disclosure and included in the term "cancer."

Also included within the term "cancer" is "solid tumor." As used herein, the term "solid tumor" refers to those conditions, such as cancer, that form an abnormal tumor mass, such as sarcomas, carcinomas, and lymphomas. Examples of solid tumors include, but are not limited to, non-small cell lung cancer (NSCLC), neuroendocrine tumors, thyomas, fibrous tumors, metastatic colorectal cancer (mCRC), and the like. In some embodiments, the solid tumor disease is an adenocarcinoma, squamous cell carcinoma, large cell carcinoma, and the like.

In some embodiments, the cancer is chosen from gastric adenocarcinoma, gastroesophageal junction (GEJ) adenocarcinoma, non-small cell lung cancer (NSCLC), breast cancer, triple-negative breast cancer (TNBC; i.e., breast cancer that tests negative for estrogen receptors (ER−), progesterone receptors (PR−), and HER2 (HER2−)), ovarian cancer, platinum-resistant ovarian cancer (PROC), pancreatic adenocarcinoma, melanoma, small cell lung cancer, and cholangiocarcinoma. In some embodiments, the cancer is chosen from non-small cell lung cancer (NSCLC), breast cancer, triple-negative breast cancer (TNBC), ovarian cancer, platinum-resistant ovarian cancer (PROC), pancreatic adenocarcinoma, melanoma, small cell lung cancer, and cholangiocarcinoma. In some embodiments, the cancer is chosen from platinum-resistant ovarian cancer, triple-negative breast cancer, and non-small cell lung cancer. In some embodiments, the cancer is platinum-resistant ovarian cancer. In some embodiments, the cancer is triple-negative breast cancer. In some embodiments, the cancer is non-small cell lung cancer. In some embodiments, the cancer is not gastric adenocarcinoma. In some embodiments, the cancer is not gastroesophageal junction adenocarcinoma. In some embodiments, the cancer is not gastroesophageal junction adenocarcinoma or gastric adenocarcinoma.

The terms "progress," "progressed," and "progression" as used herein refer to at least one of the following: (1) a response to prior therapy (e.g., chemotherapy) of progressive disease (PD); (2) the appearance of one or more new lesions after treatment with prior therapy (e.g., chemotherapy); and (3) at least a 5% (e.g., 10%, 20%) increase in the sum of diameters of target lesions, taking as a reference the smallest sum on study (this includes the baseline sum if that is the smallest on study).

As used herein, "re-sensitizing" means making subjects who were previously resistant, non-responsive, or somewhat responsive to a prior therapy (e.g., chemotherapy) regimen sensitive, responsive, or more responsive to that prior therapy (e.g., chemotherapy) regimen.

As used herein, the term "at least one compound of formula (I)" means a compound chosen from compounds having formula (I)

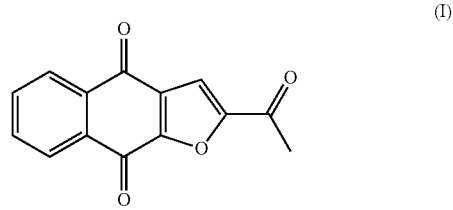 [SMILES: CC(=O)c1cc2c(o1)C(=O)c1ccccc1C2=O]

prodrugs, derivatives, pharmaceutically acceptable salts of any of the foregoing, and solvates of any of the foregoing. In some embodiments, prodrugs and derivatives of compounds having formula (I) are Stat3 inhibitors. Non-limiting examples of prodrugs of compounds having formula (I) are the phosphoric ester and phosphoric diester described in U.S. pre-grant Publication No. 2012/0252763 as compound numbers 4011 and 4012 and also suitable compounds described in in U.S. Pat. No. 9,150,530. Non-limiting examples of derivatives of compounds having formula (I) include the derivatives disclosed in U.S. Pat. No. 8,977,803. The disclosures of U.S. pre-grant Publication No. 2012/0252763 and U.S. Pat. Nos. 9,150,530 and 8,977,803 are incorporated herein by reference in their entireties.

Compounds having formula (I), shown below,

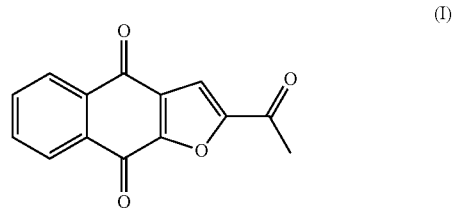 [SMILES: CC(=O)c1cc2c(o1)C(=O)c1ccccc1C2=O]

may also be known as 2-acetylnaphtho[2,3-b]furan-4,9-dione, napabucasin, or BB1608 and include tautomers thereof.

Suitable methods of preparing 2-acetylnaphtho[2,3-b]furan-4,9-dione, including its crystalline forms and additional cancer stemness inhibitors, are described in the co-owned PCT applications published as WO 2009/036099, WO 2009/036101, WO 2011/116398, WO 2011/116399, and WO 2014/169078; the contents of each application is incorporated herein by reference.

The term "salt(s)," as used herein, includes acidic and/or basic salts formed with inorganic and/or organic acids and bases. As used herein, the term "pharmaceutically acceptable salt" refers to those salts which are, within the scope of sound medical judgment, suitable for use in contact with the tissues of subjects without undue toxicity, irritation, allergic response and/or the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19.

Pharmaceutically acceptable salts may be formed with inorganic or organic acids. Non-limiting examples of suitable inorganic acids include hydrochloric acid, hydrobromic acid, phosphoric acid, sulfuric acid, and perchloric acid. Non-limiting examples of suitable organic acids include acetic acid, oxalic acid, maleic acid, tartaric acid, citric acid, succinic acid, and malonic acid. Other non-limiting examples of suitable pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid.

Salts may be prepared in situ during the isolation and purification of the disclosed compound, or separately, such as by reacting the compound with a suitable base or acid, respectively. Non-limiting examples of pharmaceutically acceptable salts derived from bases include alkali metal, alkaline earth metal, ammonium and $N^+(C_{1-4}alkyl)_4$ salts. Non-limiting examples of suitable alkali or alkaline earth metal salts include sodium, lithium, potassium, calcium, magnesium, iron, zinc, copper, manganese, and aluminum salts. Further non-limiting examples of suitable pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. Non-limiting examples of suitable organic bases from which salts may be derived include primary amines, secondary amines, tertiary amines, substituted amines including naturally occurring substituted amines, cyclic amines, and basic ion exchange resins, such as isopropylamine, trimethylamine, diethylamine, triethylamine, tripropylamine, and ethanolamine. In some embodiments, pharmaceutically acceptable base addition salts can be chosen from ammonium, potassium, sodium, calcium, and magnesium salts.

The term "solvate" represents an aggregate that comprises one or more molecules of a compound of the present disclosure with one or more molecules of a solvent or solvents. Solvates of the compounds of the present disclosure include, for example, hydrates.

In some embodiments, the at least one paclitaxel compound is administered once weekly as an IV infusion. In some embodiments, the at least one paclitaxel compound is administered at about 80 mg/m$^2$ weekly for 3 out of every 4 weeks.

The at least one compound disclosed herein may be in the form of a pharmaceutical composition. In some embodiments, the pharmaceutical compositions may comprise the at least one compound of formula (I) and at least one pharmaceutically acceptable carrier. In some embodiments, the pharmaceutical compositions may comprise one or more compounds and at least one pharmaceutically acceptable carrier, where the one or more compounds are capable of being converted into the at least one compound of formula (I) in a subject (i.e., a prodrug).

The term "carrier" as used herein means a pharmaceutically acceptable material, composition or vehicle, such as, for example, a liquid or solid filler, diluent, excipient, solvent or encapsulating material involved in or capable of carrying or transporting the subject pharmaceutical compound from one organ, or portion of the body, to another organ, or portion of the body. Each carrier must be "acceptable" in the sense of being compatible with the other ingredients of the formulation and not injurious to the patient. Non-limiting examples of pharmaceutically acceptable carriers, carriers, and/or diluents include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers, and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

In some embodiments, the at least one compound may be administered in an amount ranging from about 160 to about 1500 mg. In some embodiments, the at least one compound may be administered in an amount ranging from about 160 to about 1000 mg. In some embodiments, the at least one compound may be administered in an amount ranging from about 300 mg to about 700 mg. In some embodiments, the at least one compound may be administered in an amount ranging from about 700 mg to about 1200 mg. In some embodiments, the at least one compound may be administered in an amount ranging from about 800 mg to about 1100 mg. In some embodiments, the at least one compound may be administered in an amount ranging from about 850 mg to about 1050 mg. In some embodiments, the at least one compound may be administered in an amount ranging from about 960 mg to about 1000 mg. In some embodiments, the total amount of the at least one compound is administered once daily. In some embodiments, the at least one compound is administered in a dose of about 480 mg daily. In some embodiments, the at least one compound is administered in administered in a dose of about 960 mg daily. In some embodiments, the at least one compound is administered in a dose of about 1000 mg daily. In some embodiments, the total amount of the at least one compound is administered in divided doses more than once daily, such as twice daily (BID) or more often. In some embodiments, the at least one compound may be administered in an amount ranging from about 80 to about 750 mg twice daily. In some embodiments, the at least one compound may be administered in an amount ranging from about 80 to about 500 mg twice daily. In some embodiments, the at least one compound is administered in a dose of about 240 mg twice daily. In some embodiments, the at least one compound is administered in a dose of about 480 mg twice daily. In some embodiments, the at least one compound is administered in a dose of about 500 mg twice daily.

Pharmaceutical compositions disclosed herein that are suitable for oral administration may be in the form of capsules, cachets, pills, tablets, lozenges (using a flavored basis, usually sucrose and acacia or tragacanth), powders, granules, a solution in an aqueous or non-aqueous liquid, a suspension in an aqueous or non-aqueous liquid, an oil-in-water emulsion, a water-in-oil emulsion, an elixir, a syrup, pastilles (using an inert base, such as gelatin, glycerin, sucrose, and/or acacia) and/or mouthwashes, each containing a predetermined amount of the at least one compound of the present disclosure.

A pharmaceutical composition disclosed herein may be administered as a bolus, electuary, or paste.

Solid dosage forms for oral administration (capsules, tablets, pills, dragees, powders, granules and the like) may be mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polypropylene oxide copolymer; absorbents, such as kaolin and bentonite clay; lubricants, such a talc, calcium stearate, magnesium stearate, solid polyethylene glycols, sodium lauryl sulfate, and mixtures thereof, and coloring agents. In the case of capsules, tablets and pills, the pharmaceutical compositions may also comprise buffering agents. Solid compositions of a similar type also may be employed as fillers in soft and hard-filled gelatin capsules using such excipients as lactose or milk sugars, as well as high molecular weight polyethylene glycols and the like.

Liquid dosage forms for oral administration may include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxypropyl-β-cyclodextrin, may be used to solubilize compounds.

The pharmaceutical compositions also may include adjuvants such as wetting agents, emulsifying and suspending agents, sweetening, flavoring, coloring, perfuming and preservative agents. Suspensions, in addition to the compounds according to the disclosure, may contain suspending agents as, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions disclosed herein, for rectal or vaginal administration may be presented as a suppository, which may be prepared by mixing one or more compounds according to the present disclosure, with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the compounds of the present disclosure. Pharmaceutical compositions which are suitable for vaginal administration also may include pessaries, tampons, creams, gels, pastes, foams or spray formulations containing carriers that are known in the art to be appropriate.

Dosage forms for the topical or transdermal administration of a pharmaceutical composition or pharmaceutical tablet of the present disclosure may include powders, sprays, ointments, pastes, creams, lotions, gels, solutions, patches and inhalants. The pharmaceutical composition or pharmaceutical tablet may be mixed under sterile conditions with a pharmaceutically acceptable carrier, and with any preservatives, buffers, or propellants which may be required.

The ointments, pastes, creams and gels may contain, in addition to the pharmaceutical composition or pharmaceutical tablet of the present disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a pharmaceutical composition or a pharmaceutical tablet of the present disclosure, excipients such as lactose, talc, silicic acid, aluminum hydroxide, calcium silicates and polyamide powder, or mixtures of these substances. Additionally, sprays may contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of the present disclosure.

Compositions suitable for parenteral administration may comprise at least one more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In various embodiments, a composition described herein includes at least one compound chosen from compounds of formula (I) and pharmaceutically acceptable salts and solvates thereof and one or more surfactants. In some embodiments, the surfactant is sodium lauryl sulfate (SLS), sodium dodecyl sulfate (SDS), or one or more polyoxylglycerides. For example, the polyoxyglyceride can be lauroyl polyoxylglycerides (sometimes referred to as Gelucire™) or linoleoyl polyoxylglycerides (sometimes referred to as Labrafil™). Examples of such compositions are shown in PCT Patent Application No. PCT/US2014/033566, the contents of which are incorporated herein in its entirety.

As noted above, the methods disclosed herein may treat at least one disorder related to aberrant Stat3 pathway activity in a subject. Aberrant Stat3 pathway activity can be identified by expression of phosphorylated Stat3 ("pStat3") or its surrogate upstream or downstream regulators.

The Stat3 pathway can be activated in response to cytokines, for example, IL-6, or by one or more tyrosine kinases, for example, EGFR, JAKs, Abl, KDR, c-Met, Src, and Her2. The downstream effectors of Stat3 include but are not limited to Bcl-xl, c-Myc, cyclinD1, Vegf, MMP-2, and survivin. The Stat3 pathway has been found to be aberrantly active in a wide variety of cancers, as shown in Table 1. Persistently active Stat3 pathway may occur in more than half of breast and lung cancers, hepatocellular carcinomas, multiple myelomas and in more than 95% of head and neck cancers. Blocking the Stat3 pathway causes cancer cell-growth arrest, apoptosis, and reduction of metastasis frequency in vitro and/or in vivo.

TABLE 1

DISEASES

| | | |
|---|---|---|
| ONCOLOGY DISEASES | Solid tumors | *Breast Cancer* (Watson, C. J. and W. R. Miller. Br. J. Cancer; 1995. 71(4): p. 840-44) *Head and Neck Cancer* (SCCHN) (Song, J. I. and J. R. Grandis. Oncogene, 2000. 19(21): p. 2489-95) *Lung Cancer* (Song, L., et al. Oncogene, 2003. 22(27): p. 4150-65) *Ovarian Cancer* (Savarese, T. M., et al. Cytokine, 2002. 17(6): p. 324-34) *Pancreatic Cancer* (Toyonaga, T., et al. Cancer Lett., 2003. 201(1): p. 107-16) *Colorectal carcinoma* (Corvinus, F. M., et al, Neoplasia, 2005. 7(6): p. 545-55) *Prostate Cancer* (Gao, B., et al. FEBS Lett., 2001. 488(3): p. 179-84) *Renal Cell carcinoma* (Buettner, R., et al. Clin. Cancer Res., 2002. 8(4): p. 945-54) *Melanoma* (Carson, W. E. Clin. Cancer Res., 1998. 4(9): p. 2219-28) *Hepatocellular carcinomas* (Darnell, J. E. Nat. Med., 2005. 11(6): p. 595-96) *Cervical Cancer* (Chen, C. L., et al. Br. J. Cancer, 2007. 96(4): p. 591-99) *Endometrial Cancer* (Chen, C. L., et al. Br. J. Cancer, 2007. 96(4): p. 591-99) *Sarcomas* (Lai, R., et al. J. Pathol., 2006. 208(5): p. 624-32; and) *Brain Tumors* (Punjabi, A. S., et al. J. Virol., 2007. 81(5): p. 2449-58) *Gastric Cancers* (Kanda, N., et al. Oncogene, 2004. 23(28): p. 4921-29) |
| | Hematologic Tumors | *Multiple Myeloma* (Puthier, D., et al. Eur. J. Immunol., 1999. 29(12): p. 3945-50) |
| | | Leukemia *HTLV-1-dependent Leukemia* (Migone, T. S., et al. Science, 1995. 269(5220): p. 79-81) *Chronic Myelogenous Leukemia* (Buettner, R., et al. Clin. Cancer Res., 2002. 8(4): p. 945-54) *Acute Myelogenous Leukemia* (Spiekermann, K., et al. Eur. J. Haematol., 2001. 67(2): p. 63-71) *Large Granular Lymphocyte Leukemia* (Epling-Burnette, P. K., et al. J. Clin. Invest., 2001. 107(3): p. 351-62) |
| | Lymphomas | *EBV-related/Burkitt's* (Weber-Nordt, R. M., et al. Blood, 1996. 88(3): p. 809-16) *Mycosis Fungoides* (Buettner, R., et al. Clin. Cancer Res., 2002. 8(4): p. 945-54) *HSV Saimiri-dependent* (T-cell) (Buettner, R., et al. Clin. Cancer Res., 2002. 8(4): p. 945-54) *Cutaneous T-cell Lymphoma* (Sommer, V. H., et al. Leukemia, 2004. 18(7): p. 1288-95) *Hodgkin's Diseases* (Buettner, R., et al. Clin. Cancer Res., 2002. 8(4): p. 945-54) *Anaplastic Large-cell Lymphoma* (Lai, R., et al. Am. J. Pathol., 2004. 164(6): p. 2251-58) |

In some embodiments, the at least one disorder may be chosen from cancers related to aberrant Stat3 pathway activity, such as gastric carcinoma, gastroesophageal junction adenocarcinoma, colorectal carcinoma, pancreatic cancer, breast cancer, ovarian cancer, fallopian tube cancer, peritoneal cancer, head and neck cancer, melanoma, cholangiocarcinoma, and lung cancer.

Recent studies have disclosed that CSCs are able to regenerate tumors. These CSCs are disclosed to be functionally linked with continued malignant growth, cancer metastasis, recurrence, and cancer drug resistance. CSCs and their differentiated progeny appear to have markedly different biologic characteristics. They persist in tumors as a distinct, but rare population. Conventional cancer drug screenings depend on measurement of the amount of tumor mass and, therefore, may not identify drugs that act specifically on the CSCs. In fact, CSCs have been disclosed to be resistant to standard chemotherapies and are enriched after standard chemotherapy treatments, which can result in refractory cancer and recurrence. CSCs have also been demonstrated to be resistant to radiotherapy. Baumann, M., et al. Nat. Rev. Cancer, 2008. 8(7): p. 545-54. The reported cancer types in which CSCs have been isolated include breast cancer, head cancer, neck cancer, lung cancer, ovarian cancer, pancreatic cancer, colorectal carcinoma, prostate cancer, melanoma, multiple myeloma, Kaposi sarcoma, Ewing's sarcoma, liver cancer, medulloblastoma, brain tumors, and leukemia. Stat3 has been identified as a CSC survival and self-renewal factor. Therefore, Stat3 inhibitors may kill CSCs and/or may inhibit CSC self-renewal.

According to some embodiments, cancer stem cell or cancer stem cells refer to a minute population of CSCs that have self-renewal capability and are tumorigenic.

Disclosed herein are methods of inhibiting, reducing, and/or diminishing CSC survival and/or self-renewal comprising administering a therapeutically effective amount of at least one pharmaceutical composition comprising at least one compound of formula (I) in combination with a therapeutically effective amount of at least one paclitaxel compound chosen from paclitaxel, pharmaceutically acceptable salts thereof, and solvates of any of the foregoing. Also disclosed herein are methods of inhibiting, reducing, and/or diminishing CSC survival and/or self-renewal comprising administering a therapeutically effective amount of at least one compound of formula (I) in combination with a therapeutically effective amount of at least one paclitaxel compound chosen from paclitaxel, pharmaceutically acceptable salts thereof, and solvates of any of the foregoing.

Also disclosed herein are methods of treating at least one cancer that is refractory to conventional chemotherapies and/or targeted therapies in a subject comprising administering a therapeutically effective amount of at least one compound of formula (I) a in combination with a therapeutically effective amount of at least one paclitaxel compound chosen from paclitaxel, pharmaceutically acceptable salts thereof, and solvates of any of the foregoing. In some embodiments, the at least one compound is included in a pharmaceutical composition.

Disclosed herein are methods of treating recurrent cancer in a subject that has failed surgery, oncology therapy (e.g., chemotherapy), and/or radiation therapy, comprising administering a therapeutically effective amount of at least one compound of formula (I) in combination with a therapeutically effective amount of at least one paclitaxel compound chosen from paclitaxel, pharmaceutically acceptable salts thereof, and solvates of any of the foregoing. In various embodiments, the at least one compound of formula (I) is included in a pharmaceutical composition.

Also disclosed herein are methods of treating or preventing cancer metastasis in a subject, comprising administering a therapeutically effective amount of at least one compound of formula (I) in combination with a therapeutically effective amount of at least one paclitaxel compound chosen from paclitaxel, pharmaceutically acceptable salts thereof, and solvates of any of the foregoing. In various embodiments, the at least one compound of formula (I) is included in a pharmaceutical composition.

Disclosed herein are methods of treating cancer in a subject comprising administering a therapeutically effective amount of at least one compound of formula (I) in combination with a therapeutically effective amount of at least one paclitaxel compound chosen from paclitaxel, pharmaceutically acceptable salts thereof, and solvates of any of the foregoing. In various embodiments, the at least one compound of formula (I) is included in a pharmaceutical composition.

In some embodiments, the cancer may be chosen from gastric and gastroesophageal adenocarcinoma, advanced gastric and gastroesophageal junction adenocarcinoma, colorectal adenocarcinoma, breast cancer, ovarian cancer, head and neck cancer, melanoma, lung cancer, cholangiocarcinoma, and pancreatic cancer. In some embodiments, the cancer may be chosen from breast cancer, ovarian cancer, head and neck cancer, melanoma, lung cancer, cholangiocarcinoma, and pancreatic cancer. In some embodiments, the cancer is not gastric or gastroesophageal junction adenocarcinoma. In some embodiments, the cancer is metastatic pancreatic adenocarcinoma. In some embodiments, the cancer is advanced triple negative breast cancer. In some embodiments, the cancer is advanced non-small cell lung cancer. In some embodiments, the cancer is platinum resistant ovarian cancer. In some embodiments, the cancer is cholangiocarcinoma.

In some embodiments, the cancer may be advanced. In some embodiments, the cancer may be refractory. In some embodiments, the cancer may be recurrent. In some embodiments, the cancer may be metastatic. In some embodiments, the cancer may be associated with overexpression of Stat3. In some embodiments, the cancer may be associated with nuclear β-catenin localization.

EXAMPLES

The methods disclosed herein comprise administering to a subject in need thereof a therapeutically effective amount of at least one paclitaxel compound chosen from paclitaxel, pharmaceutically acceptable salts thereof, and solvates of any of the foregoing and at least one compound of formula (I).

Example 3

The effects of 2-acetylnaphtho[2,3-b]furan-4,9-dione, a compound of formula (I), in combination with paclitaxel in patients with heavily pretreated metastatic pancreatic adenocarcinoma were studied in a phase Ib/II extension study to assess the safety, tolerability, and preliminary anti-cancer activity of the combination disclosed herein.

In the open label phase Ib dose-escalation study, the safety, tolerability and recommended phase 2 dose (RP2D) of 2-acetylnaphtho[2,3-b]furan-4,9-dione in combination with paclitaxel were assessed in adult patients with advanced solid tumors.

The phase II clinical study enrolled patients to disease-specific cohorts to determine the preliminary anti-cancer activity of 2-acetylnaphtho[2,3-b]furan-4,9-dione in combination with paclitaxel.

A sample size of 40 in each cohort set the bounds of the 90% CI at +10% to 14%, assuming a disease control rate (DCR) of 60% to 80%.

In total, 41 patients with heavily pre-treated pancreatic adenocarcinoma aged 38-82 were enrolled in the phase Ib/II extension study (see Table 2). As shown in Table 3, these patients received a median of 2 prior lines of treatment including FOLFIRINOX (71%), gemcitabine/nab-paclitaxel (44%), or both (37%). Most patients had failed the gemcitabine/nab-paclitaxel and/or FOLFIRINOX treatment. Overall, prior therapy included gemcitabine (90%), a thymidylate synthetase inhibitor (e.g., fluorouracil (5-FU) and capecitabine) (81%), platinum (76%), irinotecan (73%), and taxane (44%).

TABLE 2

| Demographics (N = 41) | | |
| --- | --- | --- |
| Age | | |
| Median | 65 | yrs |
| Range | 38-82 | yrs |
| | N | % |
| Gender | | |
| Female | 19 | 46% |
| Male | 22 | 54% |
| Karnofsky | | |
| 90% | 20 | 49% |
| 80% | 15 | 37% |
| 70% | 4 | 10% |
| ECOG | | |
| 1 | 2 | 5% |
| Race | | |
| Caucasian | 33 | 80% |
| Black | 5 | 12% |
| Asian | 1 | 2% |
| Other | 2 | 5% |

TABLE 3

| Prior Treatments (N = 41) | | |
| --- | --- | --- |
| | N | % |
| Prior Surgery | | |
| Any surgery for cancer | 22 | 54% |
| Whipple procedure | 12 | 29% |
| Other pancreatic resection | 5 | 12% |
| Other resection | 10 | 24% |
| Prior Regimen | | |
| 1 prior | 14 | 34% |
| 2 prior | 16 | 39% |
| ≥3 prior | 11 | 27% |
| Prior Taxane | | |
| No | 23 | 56% |
| Yes | 18 | 44% |
| Prior Treatment for Cancer | | |
| FOLFIRINOX | 29 | 71% |
| Gemcitabine + Nab-paclitaxel | 18 | 44% |
| FOLFIRINOX & Gem + Nab-paclitaxel (both) | 15 | 37% |
| Any Gemcitabine | 37 | 90% |
| Any 5-FU | 33 | 80% |
| Gemcitabine plus 5-FU | 29 | 71% |
| Platinum | 31 | 76% |
| Irinotecan | 30 | 73% |
| Gemcitabine as only therapy | 6 | 15% |
| Erlotinib | 2 | 5% |

The 31 evaluable patients received 2-acetylnaphtho[2,3-b]furan-4,9-dione in combination with paclitaxel. Patients received oral administration of 2-acetylnaphtho[2,3-b]furan-4,9-dione twice daily together with paclitaxel. Specifically, 2-acetylnaphtho[2,3-b]furan-4,9-dione was administered at a starting dose of 480 mg or 500 mg BID in combination with paclitaxel at 80 mg/m$^2$ administered weekly as an IV infusion over one hour for 3 out every 4 weeks. Objective tumor response was assessed every 8 weeks using Response Evaluation Criteria In Solid Tumors (RECIST 1.1).

Figure 5:
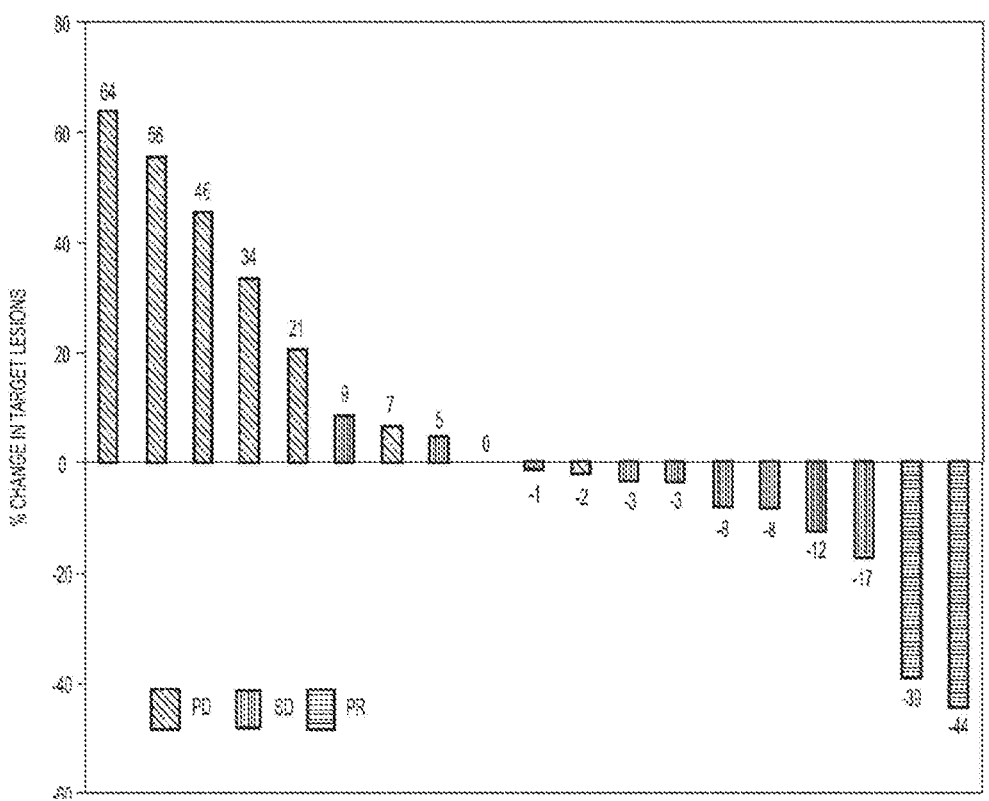
FIG. 5 shows the percent change in target lesions (best response) in evaluable taxane naïve patients (N=19) with advanced pancreatic cancer treated with 2-acetylnaphtho[2,3-b]furan-4,9-dione and paclitaxel.
Figure 6:
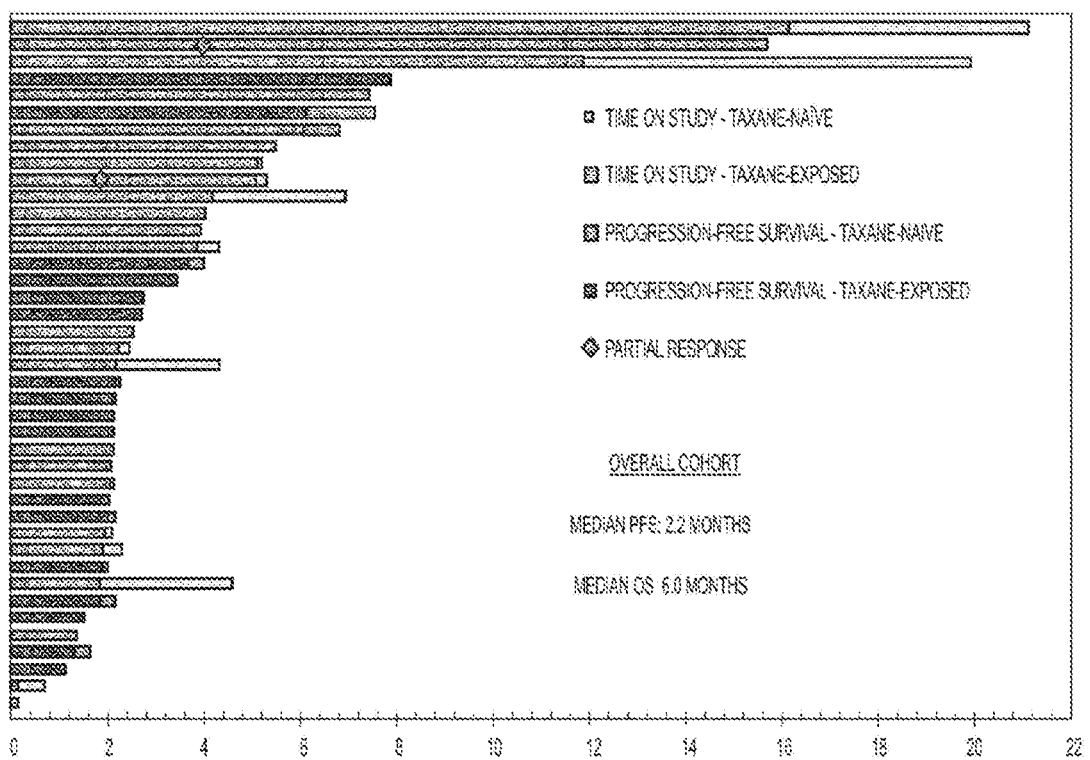
FIG. 6 shows the median progression free survival (PFS) and median overall survival (OS) of all patients (N=41), as well as each individual patient time on treatment and time without progression per RECIST, with advanced pancreatic cancer treated with 2-acetylnaphtho[2,3-b]furan-4,9-dione and paclitaxel.
Figure 7A:
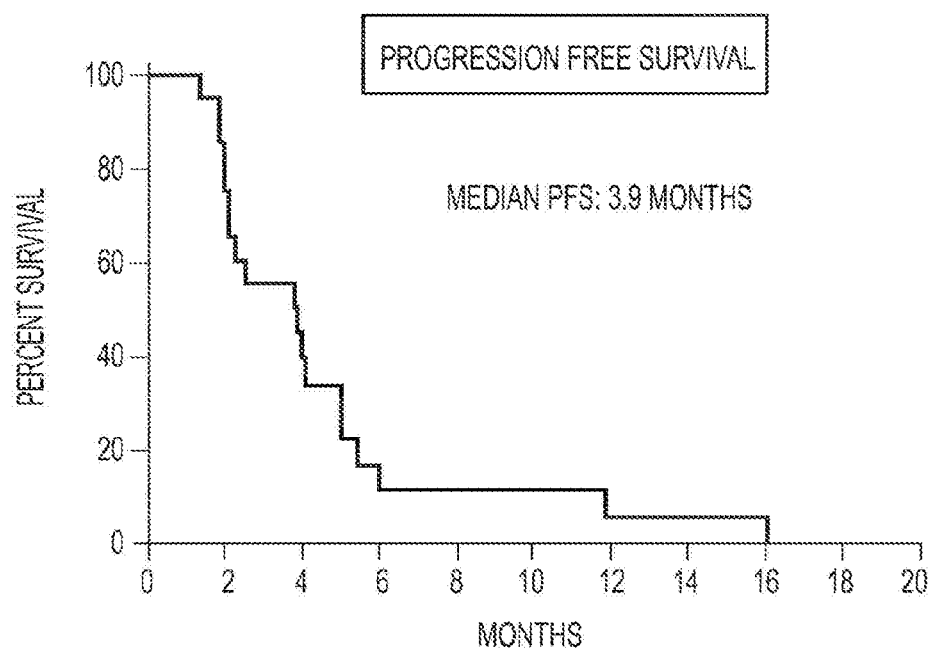
FIG. 7A and FIG. 7B show the progression free survival (PFS) (FIG. 7A) and overall survival (OS) (FIG. 7B) of all taxane-naïve patients (N=23) with advanced pancreatic cancer treated with 2-acetylnaphtho[2,3-b]furan-4,9-dione and paclitaxel.
Figure 7B:
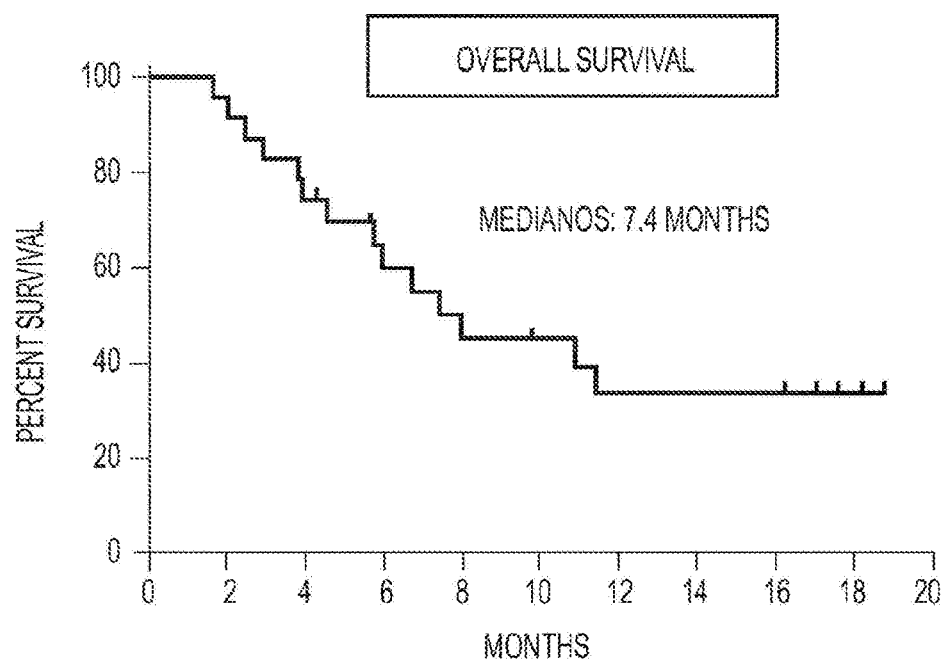

Anti-cancer activity was observed in patients with heavily pretreated metastatic pancreatic adenocarcinoma (see FIG. 5, FIG. 6, and FIG. 7). In addition, many patients continued on the treatment well after progression "per RECIST." For example, as shown in Table 4, the evaluable patients (N=31) had a 6% response rate (partial response (PR)+complete response (CR)). This same group had a 48% disease control rate (stable disease (SD)+(PR)+(CR)). The evaluable taxane-naïve patients (N=19) had an 11% response rate, 63% disease control rate (see also FIG. 5), and 4 patients experienced >50% decrease in CA19-9. Additionally, 16% of the evaluable taxane-naïve patients were progression free at 24 weeks. Overall (intention-to-treat (ITT), N=41), the median progression-free survival (mPFS) was about 10 weeks and median overall survival (mOS) was 24 weeks (see, e.g., FIG. 6). For the taxane-naïve patients (ITT, N=23), mPFS was about 16 weeks and mOS was about 30 weeks (see, e.g., Table 5 and FIG. 7). In comparison, the mOS for patients with advanced, previously treated pancreatic adenocarcinoma treated with weekly paclitaxel alone was previously reported as being about 17.5 weeks (Oettle et al, *Anticancer Drugs*, 11:635-638 (2000)).

TABLE 4

| All Evaluated Patients (N = 31*) | | | | | |
| --- | --- | --- | --- | --- | --- |
| Cohort | N | Average Lines Prior Therapy | Objective Response Rate ORR, % | Disease Control Rate DCR, % | Disease Control ≥24 weeks DCR24, % |
| Overall | 31 | 2.0 | 6% | 48% | 16% |
| Taxane Naïve | 19 | 1.6 | 11% | 63% | 16% |

*8 patients had early disease-related symptoms and 2 patients withdrew consent prior to on-study scan

TABLE 5

| All Patients - Intent to Treat (N = 41) | | | | | |
| --- | --- | --- | --- | --- | --- |
| Cohort | N | Average Lines Prior Therapy | Objective Response Rate ORR, % | Disease Control Rate DCR, % | Disease Control ≥24 weeks DCR24, % |
| Overall | 41 | 2.0 | 5% | 37% | 12% |
| Taxane Naïve | 23 | 1.6 | 9% | 52% | 13% |

This study demonstrates that 2-acetylnaphtho[2,3-b]furan-4,9-dione (480 mg or 500 mg BID) combined with weekly paclitaxel was safe, tolerable, and effectively promoted anti-tumor activity in patients with advanced pancreatic adenocarcinoma including: objective responses, CA 19-9 improvements, prolonged disease control, and surprising progression-free and overall survival.

This study further demonstrates that 2-acetylnaphtho[2,3-b]furan-4,9-dione (480 mg or 500 mg BID) combined with weekly paclitaxel effectively promoted anti-tumor activity in taxane-naïve patients and promoted notable durable disease control and prolonged overall survival in this pre-treated population.

The combination of 2-acetylnaphtho[2,3-b]furan-4,9-dione and paclitaxel was well tolerated. As shown in Table 6, the grade 3 gastrointestinal adverse events included diarrhea (N=2, 4.9%), abdominal pain (N=2, 4.9%), and nausea (N=1, 2.4%). These events were rapidly reversible.

TABLE 6

Adverse Events Related to Protocol Therapy (N = 41)

| System | Event Term | Grade 1 # | Grade 1 % | Grade 2 # | Grade 2 % | Grade 3 # | Grade 3 % |
|---|---|---|---|---|---|---|---|
| Gastrointestinal | Diarrhea | 27 | 65.9% | 12 | 29.3% | 2 | 4.9% |
|  | Nausea | 18 | 43.9% | 4 | 9.8% | 1 | 2.4% |
|  | Abdominal Pain | 11 | 26.8% | 6 | 14.6% | 2 | 4.9% |
|  | Vomiting | 7 | 17.1% | 3 | 7.3% | 0 | 0.0% |
|  | Flatulence | 1 | 2.4% | 0 | 0.0% | 0 | 0.0% |
|  | Mucositis Oral | 0 | 0.0% | 0 | 0.0% | 1 | 2.4% |
| Constitutional | Fatigue | 11 | 26.8% | 7 | 17.1% | 0 | 0.0% |
|  | Edema Limbs | 4 | 9.8% | 0 | 0.0% | 0 | 0.0% |
|  | Lymphocyte Count Decreased | 0 | 0.0% | 1 | 2.4% | 1 | 2.4% |
|  | Creatinine Increased | 1 | 2.4% | 0 | 0.0% | 0 | 0.0% |
|  | AST Increased | 1 | 2.4% | 0 | 0.0% | 0 | 0.0% |
|  | ALT Increased | 1 | 2.4% | 0 | 0.0% | 0 | 0.0% |
|  | Fever | 0 | 0.0% | 1 | 2.4% | 0 | 0.0% |
|  | Flu Like Symptoms | 0 | 0.0% | 1 | 2.4% | 0 | 0.0% |
| Metabolism - Nutrition | Anorexia | 8 | 19.5% | 3 | 7.3% | 0 | 0.0% |
|  | Dehydration | 1 | 2.4% | 2 | 4.9% | 0 | 0.0% |
|  | Hypomagnesemia | 2 | 4.9% | 0 | 0.0% | 0 | 0.0% |
|  | Hypokalemia | 1 | 2.4% | 0 | 0.0% | 0 | 0.0% |
|  | Hypoalbuminemia | 1 | 2.4% | 0 | 0.0% | 0 | 0.0% |
|  | Hyponatremia | 1 | 2.4% | 0 | 0.0% | 0 | 0.0% |
| Renal and Urinary | Urine Discoloration | 4 | 9.8% | 0 | 0.0% | 0 | 0.0% |
|  | Proteinuria | 2 | 4.9% | 0 | 0.0% | 0 | 0.0% |
| Hematologic | Anemia | 1 | 2.4% | 2 | 4.9% | 1 | 2.4% |
|  | Leukopenia | 1 | 2.4% | 0 | 0.0% | 0 | 0.0% |
| Neuro-Psychiatric | Dizziness | 1 | 2.4% | 1 | 2.4% | 0 | 0.0% |
|  | Peripheral Motor Neuropathy | 1 | 2.4% | 0 | 0.0% | 0 | 0.0% |
| Skin | Rash Maculo-Papular | 2 | 4.9% | 0 | 0.0% | 0 | 0.0% |
| Injury | Fall | 1 | 2.4% | 0 | 0.0% | 0 | 0.0% |
| Musculoskeletal | Arthralgia | 1 | 2.4% | 0 | 0.0% | 0 | 0.0% |
| Vascular | Hypotension | 1 | 2.4% | 0 | 0.0% | 0 | 0.0% |
| Other | Mucositis, NOS | 0 | 0.0% | 1 | 2.4% | 0 | 0.0% |

In sum, the disclosed combination therapy provided for effective anticancer activity and demonstrated the recommended phase 2 dose (PR2D) of 2-acetylnaphtho[2,3-b]furan-4,9-dione was 480 mg BID.

Example 4

The effects of 2-acetylnaphtho[2,3-b]furan-4,9-dione in combination with paclitaxel in patients with metastatic triple negative breast cancer (TNBC) who progressed on prior systemic therapy (including prior taxanes) were studied in a phase Ib/II study to assess the combination's safety, tolerability, and preliminary anti-cancer activity.

Patients received oral administration of 2-acetylnaphtho[2,3-b]furan-4,9-dione twice daily together with paclitaxel. For example, 2-acetylnaphtho[2,3-b]furan-4,9-dione was administered at a dose of 480 mg BID in combination with paclitaxel at 80 mg/m² administered weekly as an IV infusion for 3 out every 4 weeks.

A sample size of 40 set the bounds of the 90% CI at +10% to 14%, assuming a disease control rate (DCR) of 60% to 80%. In this example, DCR was the proportion of patients with stable disease (SD) for at least 8 weeks, or objective partial (PR) or complete response (CR) per RECIST 1.1.

The 35 enrolled patients received a median of 4 prior lines of therapy, including 33 patients (94%) who had progressed on prior taxane-based regimens.

The combination of 2-acetylnaphtho[2,3-b]furan-4,9-dione together with paclitaxel demonstrated anti-cancer activity in patients with TNBC. For the evaluable patients (N=32), for example, the disease control rate (DCR) was 63% and overall response rate (ORR) was 19%.

For the intent to treat population (N=35), the median progression-free survival (mPFS) was 10.6 weeks and median overall survival (mOS) was 37 weeks.

The combination of 2-acetylnaphtho[2,3-b]furan-4,9-dione plus weekly paclitaxel was well tolerated without dose-limiting toxicity. This therapy also exhibited a safety profile similar to that of each regimen as monotherapy. Grade 3 adverse events were rapidly reversible and included diarrhea (N=3), as well as nausea, vomiting, anorexia, abdominal pain, and fatigue (N=1 each).

This data shows 2-acetylnaphtho[2,3-b]furan-4,9-dione plus weekly paclitaxel was safe, tolerable, and surprisingly produced promising signs of anti-cancer activity in patients with heavily pretreated TNBC who had progressed following treatment with taxane-based regimens. Without being limited to any particular theory, the presence of 2-acetylnaphtho[2,3-b]furan-4,9-dione appeared to re-sensitize the patients to the paclitaxel treatment even when these patients had developed or started to develop resistance to taxane-based regimens.

In addition, patients were examined to determine whether cancer stem cell biomarkers were predictive of treatment outcome. Patients who were positive for the cancer stem cell marker pStat3 consistently exhibited longer median progression-free survival (PFS) and overall survival (OS) when treated with 2-acetylnaphtho[2,3-b]furan-4,9-dione in combination with paclitaxel compared to patients who were negative for pStat3. Without being limited to any particular theory, it would appear that pStat3 served as a predictive biomarker for prolonged survival.

Example 5

The effects of 2-acetylnaphtho[2,3-b]furan-4,9-dione in combination with paclitaxel in patients with epithelial ovarian, fallopian tube, or peritoneal cancer were studied in a phase Ib/II study to assess the combination's safety, tolerability, and preliminary anti-cancer activity. A recommended phase 2 dose (RP2D) expansion study of 2-acetylnaphtho[2,3-b]furan-4,9-dione in combination with paclitaxel included patients with platinum resistant ovarian cancer (PROC). This study enrolled patients with advanced epithelial ovarian, fallopian tube, or peritoneal cancer who progressed on a prior taxane-based regimen, and who were resistant or refractory to platinum therapy.

Patients received oral administration of 2-acetylnaphtho[2,3-b]furan-4,9-dione twice daily together with paclitaxel. Specifically, 2-acetylnaphtho[2,3-b]furan-4,9-dione was administered at a dose of 240 mg to 480 mg BID in combination with paclitaxel at 80 mg/m$^2$ administered weekly as an IV infusion 3 out every 4 weeks.

A sample size of 40 set the bounds of the 90% CI at +10% to 14%, assuming a disease control rate (DCR) of 60% to 80%. In this example, DCR was the proportion of patients with stable disease (SD) for at least 8 weeks, or objective partial (PR) or complete response (CR) per RECIST 1.1.

In total, 56 patients were enrolled after a median 4 prior lines of therapy, including prior taxanes ($^{92}$% paclitaxel only, 4% docetaxel only, 4% paclitaxel and docetaxel).

Anti-cancer activity was observed, as the evaluable patients (N=40) had a 68% DCR. Moreover, 40% of the patients experienced tumor regression and the overall response rate (ORR) (PR+CR) was 25%, including 1 patient with CR. Prior to being evaluated, 2 patients withdrew due to neuropathy, 6 for other adverse events, 5 for deterioration, 2 for non-compliance, and 1 for myocardial infarction (unrelated).

In the intent to treat (ITT) patients (N=56), DCR was 48% and overall response rate was 18%. Additionally, the median progression-free survival (mPFS) was 15 weeks and median overall survival (mOS) was 38 weeks.

In patients with up to 2 prior lines of therapy (N=11), the overall response rate was 45%.

The combination of 2-acetylnaphtho[2,3-b]furan-4,9-dione and paclitaxel was well tolerated without dose-limiting toxicity and the safety profile was similar to that of each regimen as monotherapy. Grade 3 adverse events included rapidly-reversible diarrhea (18%), vomiting (7%), abdominal pain (7%), nausea (5%), dehydration (<4%), and fatigue (<4%). Eighty percent (80%) of patients with grade 3 adverse events continued the study at a reduced dose.

Figure 8A:
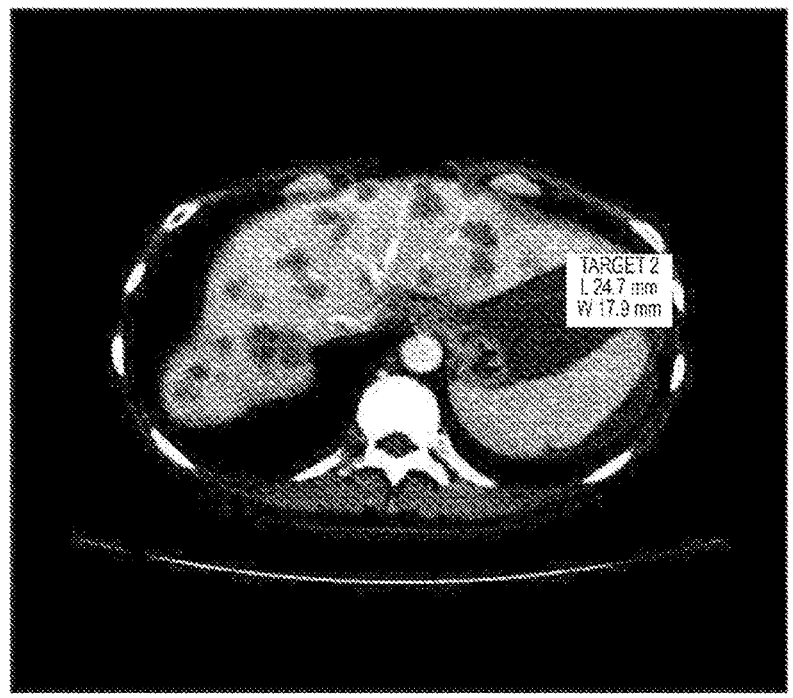
FIG. 8A and FIG. 8B show CT scans of a patient before and 16 weeks after receiving an exemplary treatment.
Figure 8B:
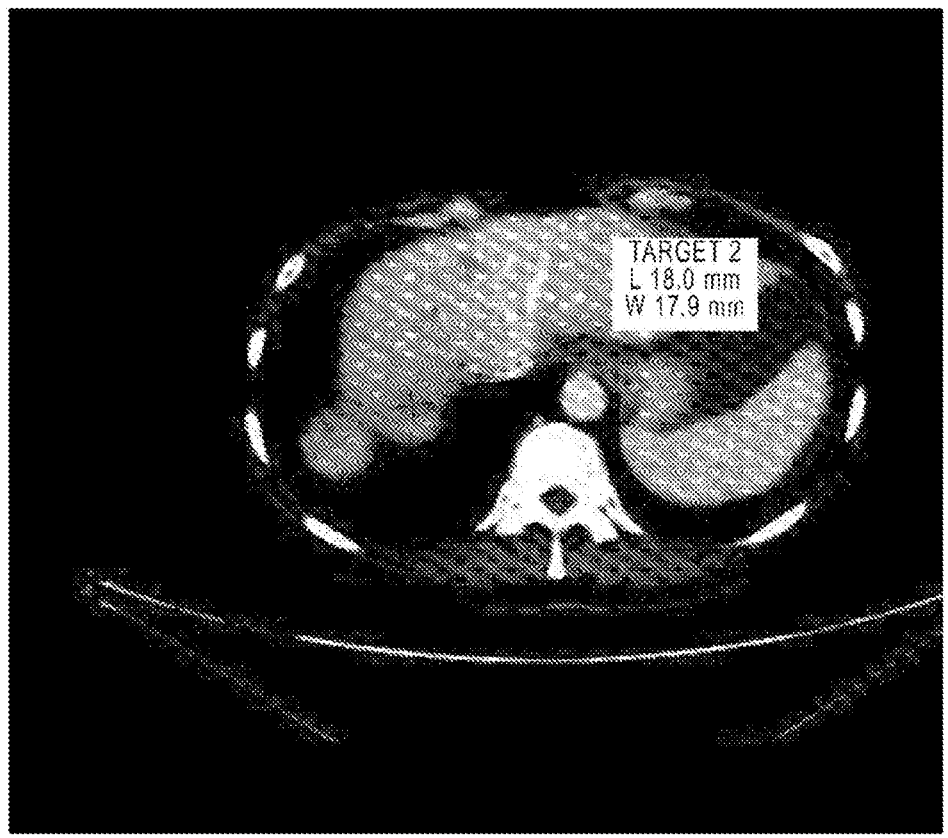

In addition, among the patients in the clinical trial, one with marked liver metastasis, profound ascites, and a CA-125 of 2000 (FIG. 8A) showed 28% regression at the 8$^{th}$ week and 49% regression at the 16$^{th}$ week (FIG. 8B) and a CA-125 of 102 at the 16$^{th}$ week.

Accordingly, 2-acetylnaphtho[2,3-b]furan-4,9-dione at a dose of 240 to 480 mg BID was safely combined with weekly paclitaxel to promote anti-cancer activity. Specifically, the disclosed combination demonstrated acceptable tolerability in patients with heavily pretreated ovarian cancer, and surprisingly included patients with heavily pre-treated PROC that had progressed on prior taxane-based regimens. Furthermore, complete and partial response, durable disease control, prolonged progression free survival, and overall survival was observed. Without being limited to any particular theory, the presence of 2-acetylnaphtho[2,3-b]furan-4,9-dione appeared to re-sensitize the patients to the paclitaxel treatment even when these patients had developed or started to develop resistance to taxane-based regimens.

Example 6

The effects of 2-acetylnaphtho[2,3-b]furan-4,9-dione in combination with paclitaxel were clinically evaluated. In a phase Ib dose escalation study in patients with advanced solid tumors, 2-acetylnaphtho[2,3-b]furan-4,9-dione plus weekly paclitaxel was well tolerated. Phase II accrual to disease-specific cohorts included patients with advanced, heavily pre-treated metastatic non-small cell lung cancer (NSCLC).

Patients with metastatic squamous or non-squamous NSCLC who had progressed on prior systemic therapy were enrolled to assess the safety, tolerability, and preliminary anti-cancer activity of 2-acetylnaphtho[2,3-b]furan-4,9-dione plus weekly paclitaxel.

Patients received oral administration of 2-acetylnaphtho[2,3-b]furan-4,9-dione twice daily together with paclitaxel. For example, 2-acetylnaphtho[2,3-b]furan-4,9-dione was administered at a starting dose of 240 mg BID in combination with paclitaxel at 80 mg/m$^2$ administered weekly as an IV infusion 3 out every 4 weeks.

A sample size of 40 set the bounds of the 90% CI at +10% to 14%, assuming a disease control rate (DCR) of 60% to 80%. In this example, DCR was the proportion with patients with stable disease (SD) for at least 8 weeks, or objective partial (PR) or complete response (CR) per RECIST 1.1.

In this study, 27 patients enrolled with a median number of 3 prior lines of systemic treatment. Twenty-six (26) of the enrolled patients (96%) had received prior taxane-based therapy. All of those patients had progressed on the prior taxane therapy.

The combination treatment disclosed herein exhibited anti-cancer activity. For the evaluable patients (N=19), the DCR was 79%. Additionally, 37% of the patients experienced tumor regression and the objective partial response (PR) was 16%.

For evaluable non-squamous patients (N=15), the DCR was 87%. Tumor regression occurred in 47% of the patients and PR in 20%.

Overall, DCR was 56% in the intent to treat (ITT) patients (N=27). Tumor regression occurred in 26% of the patients and PR in 11%. The median progression free survival (mPFS) was 16 weeks and median overall survival (mOS) was 34 weeks.

For non-squamous patients (intention-to-treat (ITT), N=22), mPFS was 17 weeks and mOS was 37 weeks.

The combination treatment disclosed herein was well tolerated. Related grade 3 adverse events, including diarrhea (N=1) and hyponatremia (N=1), were rapidly reversible.

In summary, 2-acetylnaphtho[2,3-b]furan-4,9-dione at a starting dose of 240 mg BID in combination with paclitaxel resulted in anti-cancer activity. Specifically, objective response, tumor regression, durable disease control, prolonged progression free survival, and overall survival were observed in patients with heavily pretreated NSCLC. Accordingly, these results demonstrated the safety, tolerability, and anti-cancer activity of 2-acetylnaphtho[2,3-b]furan- 4,9-dione in combination with paclitaxel in taxane refractory patients. Without being limited to any particular theory, the presence of 2-acetylnaphtho[2,3-b]furan-4,9-dione appeared to re-sensitize the patients to the paclitaxel treatment even when these patients had developed or started to develop resistance to taxane-based regimens.

In addition, patients were examined to determine whether cancer stem cell biomarkers were predictive of treatment outcome. Patients who were positive for the cancer stem cell marker pStat3 consistently exhibited longer survival (OS) when treated with 2-acetylnaphtho[2,3-b]furan-4,9-dione in combination with paclitaxel compared to patients who were negative for pStat3. Without being limited to any particular theory, it would appear that pStat3 served as a predictive biomarker for prolonged survival.

Example 7

The effects of 2-acetylnaphtho[2,3-b]furan-4,9-dione in combination with paclitaxel in patients with melanoma, small cell lung cancer, or cholangiocarcinoma were studied in a phase Ib/II study to assess the combination's safety, tolerability, and preliminary anti-cancer activity. A recommended phase 2 dose (RP2D) expansion study of 2-acetylnaphtho[2,3-b]furan-4,9-dione in combination with paclitaxel included patients with these cancers. This study enrolled patients with advanced melanoma, small cell lung cancer, or cholangiocarcinoma.

Patients received oral administration of 2-acetylnaphtho[2,3-b]furan-4,9-dione twice daily together with paclitaxel. Specifically, 2-acetylnaphtho[2,3-b]furan-4,9-dione was administered at a dose of 240 mg to 480 mg BID in combination with paclitaxel at 80 mg/m$^2$ administered weekly as an IV infusion 3 out every 4 weeks.

A sample size of 40 set the bounds of the 90% CI at +10% to 14%, assuming a disease control rate (DCR) of 60% to 80%. In this example, DCR was the proportion of patients with stable disease (SD) for at least 8 weeks, or objective partial (PR) or complete response (CR) per RECIST 1.1.

The patients with melanoma, small cell lung cancer, and cholangiocarcinoma showed evaluable DCRs of 73%, 38%, and 41%, respectively; and the patients with melanoma and small cell lung cancer showed evaluable ORR of 9% and 14%, respectively. Among the patients with small cell lung cancer, 29% of the evaluable patients showed regression.

Example 8

Napabucasin is a firstin-class cancer stemness inhibitor, identified by its ability to inhibit STAT3-driven gene transcription and spherogenesis of cancer stem cells (Li et al PNAS 112 (6):1839, 2015). Synergistic antitumor activity of napabucasin plus paclitaxel was observed in pre-clinical and early clinical testing. The STAT3 pathway is considered important in thymic carcinoma and thymoma, rare cancers with few treatment options. In 1st line, the objective response rate (ORR, partial response [PR]+complete response [CR] per RECIST) with carboplatin-paclitaxel was 22% in thymic carcinoma and 43% in thymoma (Gemma, 2011). A phase 1b cohort was established to evaluate safety and preliminary signs of activity of napabucasin plus paclitaxel in these patients.

Patients with previously-treated advanced thymoma or thymic carcinoma were enrolled with napabucasin (240-480 mg orally twice daily) plus paclitaxel (80 mg/m2 IV weekly for 3 of every 4 weeks). Adverse events were evaluated using CTCAE v4.03 and tumor assessments were obtained every 8 wks per RECIST 1.1.

A total of 9 patients (thymic carcinoma=5, thymoma=4) with a median 3 prior lines of systemic therapy were enrolled. In thymic carcinoma, the starting napabucasin dose was 480 mg BID (n=2), and 240 mg BID (n=3). Treatment was well tolerated and 1 patient requiring dose-reduction. There were no grade 3 AEs reported. As of data cutoff, 3 patients are off-study with progression and 2 remain on treatment. PRs were observed in 4 of 5 patients (ORR=80%) and the median time on treatment is >7.0 mo. In thymoma, 4 patients received napabucasin 240 mg BID. AEs included grade 3 diarrhea and dehydration in 1 pt. As of data cutoff, 1 pt was off-study with progression, 2 died (perforated bowel; autoimmune myocarditis secondary to Issac's syndrome), and 1 pt remains on treatment. PR was observed in 1 pt (ORR 25%).

Napabucasin plus weekly paclitaxel has demonstrated clinical safety and encouraging signs of antitumor activity in patients with advanced thymic carcinoma and thymoma. Further clinical evaluation of the combination regimen is warranted in this population.

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described accordingly, all suitable modifications and equivalents may be resorted to, falling within the scope of the present disclosure.

We claim:

1. A method for treating a advanced thymoma or thymic carcinoma in a human subject comprising administering to the subject a therapeutically effective amount of a compound of formula (I):

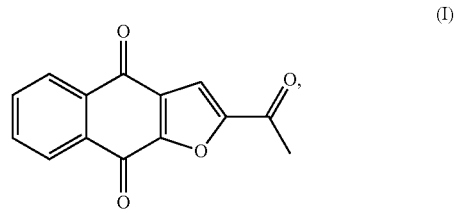 [SMILES: CC(=O)c1cc2c(o1)C(=O)c1ccccc1C2=O]

wherein the compound of Formula (I) is administered orally to the subject at a total daily dose of about 480 mg; and
a therapeutically effective amount of paclitaxel,
wherein paclitaxel is administered weekly.

2. The method according to claim 1, wherein the compound of formula (I) and paclitaxel are administered to a subject simultaneously or sequentially.

3. The method according to claim 1, wherein paclitaxel is administered at about 80 mg/m$^2$ weekly for 3 out of every 4 weeks as an infusion.

4. The method according to claim 1, wherein the compound of formula (I) is administered at a dose of about 240 mg twice daily.

5. The method according to claim 1, wherein the method is for treating thymic carcinoma.

6. The method according to claim 1, wherein the method is for treating advanced thymoma.

* * * * *

UNITED STATES PATENT AND TRADEMARK OFFICE
CERTIFICATE OF CORRECTION

PATENT NO. : 10,646,464 B2
APPLICATION NO. : 15/981406
DATED : May 12, 2020
INVENTOR(S) : Chiang Jia Li et al.

Page 1 of 1

It is certified that error appears in the above-identified patent and that said Letters Patent is hereby corrected as shown below:

In the Claims

Column 26
Claim 1, Line 38, delete "treating a" and insert --treating--.

Signed and Sealed this
Twenty-third Day of June, 2020

Andrei Iancu
*Director of the United States Patent and Trademark Office*